United States Patent [19]

Haneishi et al.

[11] Patent Number: 5,039,663
[45] Date of Patent: Aug. 13, 1991

[54] ANTIBIOTICS CALLED "MUREIDOMYCINS A, B, C, AND D" AND THEIR THERAPEUTIC USE

[75] Inventors: Tatsuo Haneishi; Masatoshi Inukai; Keiko Shimizu; Fujio Isono; Yoshiharu Sakaida; Takeshi Kinoshita, all of Tokyo, Japan

[73] Assignee: Sankyo Company Limited, Tokyo, Japan

[21] Appl. No.: 253,450

[22] Filed: Oct. 4, 1988

Related U.S. Application Data

[63] Continuation-in-part of Ser. No. 51,665, May 18, 1987, abandoned.

[30] Foreign Application Priority Data

May 20, 1986 [JP] Japan .................................. 61-115639
Jun. 13, 1986 [JP] Japan .................................. 61-137567

[51] Int. Cl.$^5$ ...................... A61K 37/02; C07K 5/08; C07K 5/10; C07K 7/06
[52] U.S. Cl. ...................................... 514/18; 514/17; 514/19; 530/329; 530/330; 530/331
[58] Field of Search ...................... 530/329, 330, 331; 514/17–19

[56] References Cited

U.S. PATENT DOCUMENTS 4,670,542  6/1987  Benz et al. ........................... 530/331
4,722,924  2/1988  Baldwin .............................. 530/331
4,748,155  5/1988  Sisto et al. ............................ 514/18

Primary Examiner—Lester L. Lee
Attorney, Agent, or Firm—Frishauf, Holtz, Goodman & Woodward, P.C.

[57] ABSTRACT

Novel compounds, called mureidomycins A, B, C and D, may be prepared by cultivation of a suitable microorganism of the genus Streptomyces, especially *Streptomyces flavidovirens* SANK 60486 (FERM P-8636, FERM BP-1347). These represent a wholly new class of antibiotics, which are valuable in the treatment of infections caused by a variety of bacteria, notably of the genus Pseudomonas.

25 Claims, 14 Drawing Sheets

ANTIBIOTICS CALLED "MUREIDOMYCINS A, B, C, AND D" AND THEIR THERAPEUTIC USE

This application is a continuation-in-part of application Ser. No. 07/051,665, filed May 18, 1987 now abandoned.

BACKGROUND TO THE INVENTION

The present invention relates to certain novel antibiotics, which we have named "mureidomycins A, B, C and D", and also provides a method for preparing them and an antibacterial composition containing at least one of them as the active ingredient.

As resistance to conventional antibiotics becomes increasingly established in common strains of pathogenic bacteria, the need for a wider variety of antibiotics for use in the fight against such bacteria becomes ever more crucial. Although this need can be, and sometimes is, met by chemical modification of existing classes of antibiotic, the discovery of a wholly new class of antibiotic leads to exciting possibilities in the treatment of diseases caused by pathogenic bacteria.

We have now discovered a new class of antibiotics, which we have named the "mureidomycins" and have isolated 4 members of this class, which we have called "mureidomycins A, B, C and D", from the fermentation broth produced by a newly isolated microorganism named strain SANK 60486. This microorganism was isolated from soil and identified to be a strain of the species Streptomyces. We have found that these new antibiotics are particularly effective against gram-negative bacteria, most especially strains of the genus Pseudomonas.

BRIEF SUMMARY OF INVENTION

It is, therefore an object of the present invention to provide, as a new composition of matter, certain new compounds having useful antibacterial activities.

It is a further object of the invention to provide a pharmaceutical composition containing at least one such compound as the active component and a method for the treatment or prophylaxis of bacterial infections employing at least one such compound as the active component.

The new compounds of the present invention are mureidomycins A, B, C and D which are represented by the following structural formula:

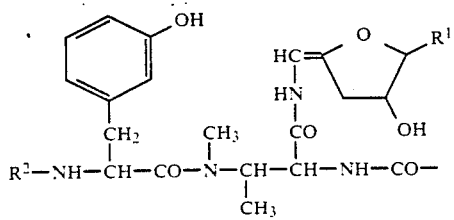

-continued

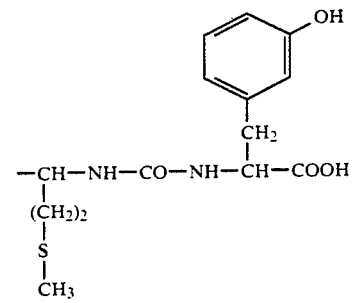

For mureidomycin A, $R^1$ represents a uracil group and $R^2$ represents a hydrogen atom; mureidomycin B, $R^1$ represents a dihydrouracil group and $R^2$ represents a hydrogen atom; mureidomycin C, $R^1$ represents a uracil group and $R^2$ represents a glycine group; and mureidomycin D, $R^1$ represents a dihydrouracil group and $R^2$ represents a glycine group.

The mureidomycins are further identified and defined by their physico-chemical properties, as follows:

Mureidomycin A has the following physico-chemical properties:

1) Character and appearance: Amphoteric, soluble in water, white powder;
2) Specific rotation: $[\alpha]_D^{25} = +40.9°$ (c=0.69, 50% v/v aqueous methanol);
3) Elemental analysis: C, 49.73%; H, 5.65%; N, 12.08%; S, 3.40%—measured as the hydrate;
4) Molecular weight: 840 (high resolution mass spectrum), FAB MS: 841.31798 (QM+) (FAB MS is Fast Atom Bombardment Mass Spectroscopy);
5) Molecular formula: $C_{38}H_{48}N_8O_{12}S_1$;
6) Products resulting from acid hydrolysis: Uracil, m-tyrosine, 2-amino-3-N-methylaminobutyric acid;
7) Ultraviolet absorption spectrum: $\lambda_{max}$ nm ($E_1^{1\%}_{cm}$) 260 nm (348) in neutral water; 258 nm (358) in 0.01N aqueous HCl; 240 nm (499), 265 nm (330, shoulder) and 295 nm (78, shoulder) in 0.01N aqueous NaOH; the spectra are shown in FIGS. 1A and 1B of the accompanying drawings;
8) Infrared absorption spectrum (KBr), $v_{max}$ cm$^{-1}$: the spectrum measured in a KBr disk is shown in FIG. 2 of the accompanying drawings;
9) Nuclear magnetic resonance spectrum, δ ppm: the spectrum (400 MHz) was measured in dimethyl sulfoxide using TMS (tetramethylsilane) as an external standard and is shown in FIG. 3 of the accompanying drawings;
10) Solubility: Soluble in water and methanol, slightly soluble in acetone, and insoluble in ethyl acetate, chloroform and benzene;
11) Color reaction: Positive to ninhydrin, sulfuric acid, iodine, ferric chloride and Baeyer reactions;
12) Thin-layer chromatography:
Rf value; 0.36
Adsorbent; Silica gel plate (Merck, Kieselgel 60 $F_{254}$)
Developing solvent: a 4:2:1 by volume mixture of butanol, propanol and water;
13) High performance liquid chromatography:
Column: Aquasil SS 372-N (Senshu Kagaku Co.)
Developing solvent; a 200:100:100:40 by volume mixture of chloroform, isopropanol, methanol and water;
Flow rate: 1 ml/minute;
Retention time; 3.92 minutes.

Mureidomycin B has the following physico-chemical properties:

1) Character and appearance: Amphoteric, soluble in water, white powder;
2) Specific rotation: $[\alpha]_D^{23} = -7°$ (c=0.3, 50% v/v aqueous methanol);
3) Elemental analysis: C, 50.67%; H, 6.36%; N, 12.62%; S, 3.13%—measured as the hydrate;
4) Molecular weight: 842 (high resolution mass spectrum), FAB MS: 843.33289 (QM+);
5) Molecular formula: $C_{38}H_{50}N_8O_{12}S_1$;
6) Products resulting from acid hydrolysis: Dihydrouracil, m-tyrosine, 2-amino-3-N-methylaminobutyric acid;
7) Ultraviolet absorption spectrum: $\lambda_{max}$ nm ($E_1^{1\%}_{cm}$) 255 nm (194) in neutral water; 255 nm (186) in 0.1N aqueous HCl; 245 nm (325) and 295 nm (85, shoulder) in 0.1N aqueous NaOH; the spectrum is shown in FIG. 7 of the accompanying drawings;
8) Infrared absorption spectrum (KBr) $\nu_{max}$ cm$^{-1}$: the spectrum measured in a KBr disk is shown in FIG. 8 of the accompanying drawings;
9) Nuclear magnetic resonance spectrum, δ ppm: the spectrum (270 MHz) was measured in deuterium oxide using TMS as an external standard and is shown in FIG. 9 of the accompanying drawings;
10) Solubility: Soluble in water and methanol, slightly soluble in acetone and insoluble in ethyl acetate, chloroform and benzene;
11) Color reaction: Positive to ninhydrin, sulfuric acid, iodine, ferric chloride and Baeyer reactions;
12) Thin-layer chromatography:
Rf value; 0.34
Adsorbent; Silica gel plate (Merck, Kieselgel 60 $F_{254}$)
Developing solvent; a 4:2:1 by volume mixture of butanol, propanol and water;
13) High performance liquid chromatography:
Column: Aquasil SS 372-N (Senshu Kagaku Co.)
Developing solvent; a 200:100:100:40 by volume mixture of chloroform, isopropanol, methanol and water
Flow rate: 1 ml/minute;
Retention time; 3.94 minutes.

Mureidomycin C has the following physico-chemical properties:

1) Character and appearance: Amphoteric, soluble in water, white powder;
2) Specific rotation: $[\alpha]_D^{25} = +16.7°$ (c=0.57, 50% v/v aqueous methanol);
3) Elemental analysis: C, 49.44%; H, 5.50%; N, 12.53%; S, 3.09%—measured as the hydrate;
4) Molecular weight: 897 (high resolution mass spectrum), FAB MS: 898.33687 (QM+);
5) Molecular formula: $C_{40}H_{51}N_9O_{13}S_1$;
6) Products resulting from acid hydrolysis: Uracil, glycine, m-tyrosine, 2-amino-3-N-methylaminobutyric acid;
7) Ultraviolet absorption spectrum: $\lambda_{max}$ nm ($E_1^{1\%}_{cm}$) 258 nm (292) in neutral water; 259 nm (312) in 0.01N aqueous HCl; 240 nm (444), 265 nm (276, shoulder) and 295 nm (72, shoulder) in 0.01N aqueous NaOH; the spectra are shown in FIGS. 4A and 4B of the accompanying drawings;
8) Infrared absorption spectrum (KBr) $\nu_{max}$ cm$^{-1}$: the spectrum measured in a KBr disk is shown in FIG. 5 of the accompanying drawings;
9) Nuclear magnetic resonance spectrum, δ ppm: the spectrum (270 MHz) was measured in deuterium oxide using TMS as an external standard and is shown in FIG. 6 of the accompanying drawings;
10) Solubility: Soluble in water and methanol, slightly soluble in acetone, and insoluble in ethyl acetate, chloroform and benzene;
11) Color reaction: Positive to ninhydrin, sulfuric acid, iodine, ferric chloride and Baeyer reactions;
12) Thin-layer chromatography:
Rf value; 0.29
Absorbent; Silica gel plate (Merck, Kieselgel 60 $F_{254}$)
Developing solvent; a 4:2:1 by volume mixture of butanol, propanol and water;
13) High performance liquid chromatography:
Column: Aquasil SS 372-N (Senshu Kagaku Co.)
Developing solvent; a 200:100:100:40 by volume mixture of chloroform, isopropanol, methanol and water
Flow rate: 1 ml/minute;
Retention time; 6.29 minutes.

Mureidomycin D has the following physico-chemical properties:

1) Character and appearance: Amphoteric, soluble in water, white powder;
2) Specific rotation: $[\alpha]_D^{23} = -30°$ (c=0.52, 50% v/v aqueous methanol);
3) Elemental analysis: C, 48.79%; H, 5.86%; N, 12.42%; S, 3.26%—measured as the hydrate;
4) Molecular weight: 899 (high resolution mass spectrum), FAB MS: 900.35617 (QM+);
5) Molecular formula: $C_{40}H_{53}N_9O_{13}S_1$;
6) Products resulting from acid hydrolysis: Dihydrouracil, glycine, m-tyrosine, 2-amino-3-N-methylaminobutyric acid;
7) Ultraviolet absorption spectrum: $\lambda_{max}$ nm ($E_1^{1\%}_{cm}$) 255 nm (191) in neutral water; 255 nm (184) in 0.1N aqueous HCl; 245 nm (346), and 295 nm (90, shoulder) in 0.1N aqueous NaOH; the spectrum is shown in FIG. 10 of the accompanying drawings;
8) Infrared absorption spectrum (KBr) $\nu_{max}$ cm$^{-1}$: the spectrum measured in a KBr disk is shown in FIG. 11 of the accompanying drawings;
9) Nuclear magnetic resonance spectrum, δ ppm: the spectrum (270 MHz) was measured in deuterium oxide using TMS as an external standard and is shown in FIG. 12 of the accompanying drawings;
10) Solubility: Soluble in water and methanol, slightly soluble in acetone and insoluble in ethyl acetate, chloroform and benzene;
11) Color reaction: Positive to ninhydrin, sulfuric acid, iodine, ferric chloride and Baeyer reactions;
12) Thin-layer chromatography:
Rf value; 0.26
Adsorbent; Silica gel plate (Merck, Kieselgel 60 $F_{254}$)
Developing solvent; a 4:2:1 by volume mixture of butanol, propanol and water;
13) High performance liquid chromatography:
Column: Aquasil SS 372-N (Senshu Kagaku Co.)
Developing solvent; a 200:100:100:40 by volume mixture of chloroform, isopropanol, methanol and water
Flow rate: 1 ml/minute;
Retention time; 7.24 minutes.

The invention also provides pharmaceutically acceptable salts and esters of the above compounds.

The invention also provides a process for producing mureidomycin A, B, C or D and salts and esters thereof by cultivating a mureidomycin A, B, C or D-producing microorganism of the genus Streptomyces in a culture medium therefor and isolating mureidomycin A, B, C or D or a salt thereof from the cultured broth and optionally salifying, desalifying or esterifying the compound thus isolated.

The invention still further provides a pharmaceutical composition comprising such a mureidomycin A, B, C or D or a salt or ester thereof in admixture with a pharmaceutically acceptable carrier or diluent.

The invention still further provides a method for the treatment or prophylaxis of bacterial infections by administering such a mureidomycin A, B, C or D or a salt or ester thereof to an animal, which may be human or non-human.

DETAILED DESCRIPTION OF INVENTION

Figure 1A:
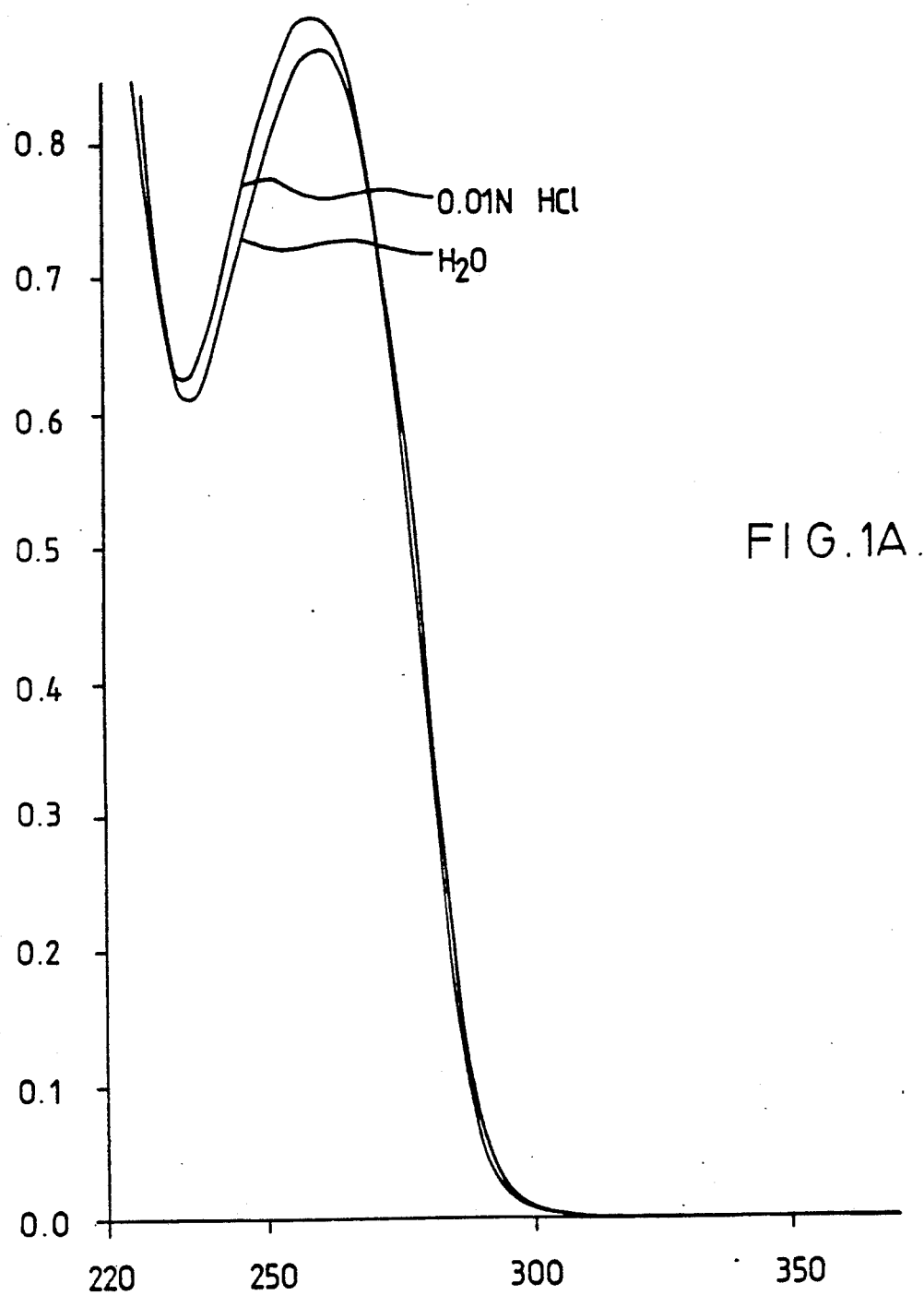
FIG. 1 shows the ultraviolet absorption spectrum of mureidomycin A.

Mureidomycins A, B, C and D and salts thereof are produced by the cultivation of a Streptomyces strain herein identified as Streptomyces sp. SANK 60486, and which has the following mycological properties. These characteristics were determined by cultivation on various media prescribed by the ISP (International Streptomyces Project) or with the media recommended by S. A. Waksman in Volume 2 of "The Actinomycetes", in all cases at a temperature of 28° C., except where otherwise stated.

1. MORPHOLOGICAL CHARACTERISTICS

Generally, on an agar medium, the substrate hyphae of the microorganism branch and elongate well and the aerial hyphae of the microorganism branch simply. The spore chain forms straight to curved lines. It is observed that the number of spores formed on a spore chain are mostly from ten to fifty, but may be more. The spores are elliptoidal and in size range from 0.5–0.8 $\mu m \times 0.7$–1.1 $\mu m$; they have a smooth surface. No special organs, such as wheel axle branching of the aerial hyphae, sclerotia, sporangia and the like, were observed.

2. CULTURE CHARACTERISTICS

After culturing on various kinds of culture media at 28° C. for 14 days, the properties are shown in Table 1. Representation of the color tones is shown by using the color tip numbers given in the "Guide to Color Standard" edited by Nippon Shikisai Kenkyusho.

In this Table, the following abbreviations are used: G: growth; AM: aerial mycelium; R: reverse; SP: soluble pigment.

TABLE 1

| Culture medium | Item | Properties of SANK 60486 |
| --- | --- | --- |
| Sucrose nitrate agar | G | Limited, flat, yellowish grey (1-9-10) |
|  | AM | Well formed, powdery, yellowish grey (1-9-10) |
|  | R | Pale yellowish orange (2-9-9) |
|  | SP | Not produced |
| Glucose asparagine agar | G | Good, flat, light brown (2-8-9) |
|  | AM | Well formed, powdery, pale yellowish orange (2-9-9) |
|  | R | Yellowish brown (4-7-9) |
|  | SP | Not produced |
| Glycerin asparagine agar (ISP 5) | G | Good, protuberant, pale yellowish orange (2-7-9) |
|  | AM | Plentiful, powdery, pale yellowish orange (2-9-9) |
|  | R | Yellowish brown (4-7-9) |
|  | SP | Not produced |
| Starch inorganic salt agar (ISP 4) | G | Very good, flat, pale yellowish brown (4-8-9) |
|  | AM | Plentiful, powdery, pale yellowish orange (2-9-9) |
|  | R | Pale yellowish brown (4-8-9) |
|  | SP | Not produced |
| Tyrosine agar (ISP 2) | G | Very good, flat, bright brownish grey (2-8-8) |
|  | AM | Plentiful, powdery, brownish white (1-8-6) |
|  | R | Yellowish brown (4-7-9) |
|  | SP | Not produced |
| Peptone yeast extract iron agar (ISP 6) | G | Very good, rumpled, pale yellowish brown (4-8-9) |
|  | AM | Slightly formed, white |
|  | R | Pale yellowish brown (6-7-9) |
|  | SP | Not produced |
| Nutrient agar (Difco) | G | Very good, flat, pale yellowish orange (2-9-9) |
|  | AM | Well formed, powdery, white |
|  | R | Pale yellowish orange (2-9-9) |
|  | SP | Not produced |
| Yeast germ wheat agar (ISP 2) | G | Very good, flat, pale yellowish brown (4-8-9) |
|  | AM | Plentiful, powdery, yellowish grey (2-8-10) |
|  | R | Yellowish brown (8-6-9) |
|  | SP | Not produced |
| Oatmeal agar (ISP 3) | G | Good, flat, yellowish grey (1-9-10) |
|  | AM | Plentiful, powdery, yellowish grey (1-9-10) |
|  | R | Pale yellowish brown (6-7-9) |
|  | SP | Pale yellowish brown (4-7-8 slightly) |
| Water agar | G | Limited, flat, yellowish grey (1-9-10) |
|  | AM | Limited, powdery, white |
|  | R | Pale yellowish orange (2-9-9) |
|  | SP | Not produced |
| Potato extract carrot extract agar | G | Limited, flat, pale yellowish orange (2-9-9) |
|  | AM | Well formed, powdery, pale yellowish orange (2-9-9) |
|  | R | Pale yellowish orange (2-9-9) |
|  | SP | Not produced |

3. PHYSIOLOGICAL PROPERTIES

The physiological properties of strain SANK 60486 are shown in Table 2.

TABLE 2

| Hydrolysis of starch | Positive |

TABLE 2-continued

| | |
|---|---|
| Liquefaction of gelatin | Positive |
| Reduction of nitrate salt | Positive |
| Coagulation of milk | Positive |
| Peptonization of milk | Positive |
| Temperature range of growth (culture medium 1)* | 6-34° C. |
| Sodium chloride resistance (culture medium 1)* | Growth in 7%, no growth in 10% |
| Decomposition of casein | Positive |
| Decomposition of tyrosine | Positive |
| Decomposition of xanthine | Negative |
| Productivity of melanin-like pigment | |
| (culture medium 2)* | Negative |
| (culture medium 3)* | Negative |
| (culture medium 4)* | Negative |

*Culture medium 1: yeast germ wheat agar (ISP 2);
*Culture medium 2: tryptone yeast extract broth (ISP 1);
*Culture medium 3: peptone yeast extract iron agar (ISP 6);
*Culture medium 4: tyrosine agar (ISP 7).

After culturing on Pridham Gottlieb agar medium (ISP 9) at 28° C. for 14 days, assimilability of carbon sources by strain SANK 60486 is shown in Table 3.

TABLE 3

| | |
|---|---|
| D-Glucose | + |
| L-Arabinose | + |
| D-Xylose | + |
| Inositol | − |
| D-Mannitol | + |
| D-Fructose | + |
| L-Rhamnose | + |
| Sucrose | − |
| Raffinose | − |
| Control | − |

In the above Table: + assimilable; − not assimilable.

4. CELL WALL CONSTITUTION

The cell wall of strain SANK 60486 was examined according to the method of B. Becker et al. [Applied Microbiology, 12, 421-423 (1964)]. L,L-Diaminopimelic acid and glycine were detected in it.

Identification of strain SANK 60486 was carried out in accordance with The International Streptomyces Project; Bergey's Manual of Determinative Bacteriology, 8th edition; "The Actinomycetes" edited by S. A. Waksman and other recent literature relating to the Streptomycetes.

On the basis of the above data, the strain was identified as a strain of *Streptomyces flavidovirens* and is here referred to as *Streptomyces flavidovirens* SANK 60486 (FERM P-8636).

The strain SANK 60486 has been deposited with the Fermentation Research Institute, Agency of Industrial Science and Technology, Ministry of International Trade and Industry, Japan, on Feb. 4, 1986 under the accession No. FERM P-8636 and was re-deposited in accordance with the conditions stipulated by the Budapest Treaty with said Fermentation Research Institute on Apr. 17, 1987 under the accession No. FERM BP-1347.

It has been established that strain SANK 60486 produces mureidomycins A, B, C and D. However, as is well known, the properties of microorganisms falling within the general category of the actinomycetes can vary considerably and such microorganisms can readily undergo mutation, both through natural causes and as the result of induction by artificial means. Accordingly, the process of the present invention embraces the use of any microorganism which can be classified within the genus Streptomyces and which shares with the strain SANK 60486 the characteristic ability to produce mureidomycins A, B, C and D.

The microorganism employed in the process of the present invention is preferably a strain of the species *Streptomyces flavidovirens*, and more preferably *Streptomyces flavidovirens* SANK 60486 (FERM P-8636).

The cultivation of microorganisms of the genus Streptomyces in accordance with the present invention to produce mureidomycins A, B, C and D can be performed under conditions conventionally employed for the cultivation of actinomycetes species, preferably in a liquid culture, and desirably with shaking or stirring and aeration. The nutrient medium used for the cultivation is completely conventional and contains such constituents as are commonly used in the cultivation of the actinomycetes. Specifically, the medium should contain one or more assimilable carbon sources, suitable examples of which include glucose, maltose, sucrose, mannitol, molasses, glycerol, dextrin, starch, soybean oil and cottonseed oil; one or more assimilable nitrogen sources, suitable examples of which include soybean meal, peanut meal, cottonseed meal, pharmamine, fish meal, corn steep liquor, peptone, meat extract, live yeast, pressed yeast, yeast extract, sodium nitrate, ammonium nitrate or ammonium sulfate; and one or more inorganic salts, such as sodium chloride, phosphates, calcium carbonate and trace metal salts. Where cultivation is effected in a liquid medium, it is generally desirable to incorporate an anti-foaming agent (for example, silicone oil, vegetable oil or a suitable surfactant) in the medium.

The cultivation is suitably performed at a substantially neutral pH value and at a temperature of from 20° to 37° C., more preferably at about 22° C.

The production of mureidomycins A, B, C and D as cultivation proceeds may be monitored by a variety of conventional microbiological assay techniques for monitoring the production of antibiotics (when they are produced by microbial culture) and which require little or no elaboration here. A suitable technique might be the paper disc-agar diffusion assay (using, for example, a paper disc of diameter about 8 mm produced by Toyo Kagaku Sangyo Co., Ltd) and using, for example, *Pseudomonas aeruginosa* as the test organism.

The amount of mureidomycins A, B, C and D produced normally reaches a maximum after cultivation has proceeded for 72-96 hours and it is clearly desirable to separate the mureidomycins from the culture medium no later than the time when this maximum has been reached. However, this period may vary, depending upon the cultivation conditions and techniques, and a shorter or longer period may be appropriate, depending upon the circumstances. The correct cultivation time may readily be assessed for every case by routine experiment, using suitable monitoring techniques, e.g., as described above.

Mureidomycins A, B, C and D are mainly released into the liquid portion of the cultured broth and can thus be recovered by removing solid matter, including the mycelium, for example, by filtration (preferably using a filter aid such as diatomaceous earth) or by centrifugation. They can then be recovered from the separated liquid portion by conventional techniques and, if desired, then purified and/or separated from each other.

The antibiotics, mureidomycins A, B, C and D, may be separated, collected and purified by utilizing their physico-chemical properties. For example, suitable methods include: extraction with solvents; ion-exchange through resins, for example, anion exchange resins such as Dowex SBR-P (Dow Chemical Co.) or cation exchange resins such as Dowex 50 W (Dow Chemical Co.) or IRC-50, CG-50 (Rohm & Haas Co.); chromatography through active carbon as the absorbent or through non-ionic absorption resins such as Amberlite XAD-2, XAD-4 or XAD-7 (Rohm and Hass Co.) or Diaion HP 10, HP 20, CHP 20P or HP 50 (Mitsubishi Chemical Industries, Ltd.); and chromatography through silica gel or alumina. Furthermore, separation, collection and purification of the metabolites may be performed by using any one or more of the following operations, which may be combined in any order or repeated, if desired: partition column chromatography over cellulose such as Avicel (Asahi Chemical Industry Co., Ltd.) or Sephadex LH-20 (Pharmacia Co.); gel filtration using Sephadex G-10, G-25, G-50 or G-100 (Pharmacia Co.) or Toyopearl HW-40 (Toyo Soda MFG Co., Ltd.); crystallization; and recrystallization. "Dowex", "Amberlite", "Diaion", "Avicel", "Sephadex" and "Toyopearl" are all trade marks.

Depending upon the culture conditions, mureidomycins A, B, C and D can exist in the mycelium from the culture broth and can be extracted therefrom by conventional techniques. For example, they can be extracted with a hydrophilic organic solvent (such as an alcohol or acetone), and then the solvent removed from the extract to leave a residue, which is dissolved in an aqueous medium. The mureidomycins can be extracted from the resulting solution and purified as described above.

Mureidomycins A, B, C and D are preferably separated from each other by chromatography.

Mureidomycins A, B, C and D thus obtained have the physical and chemical properties described above.

Since mureidomycins A, B, C and D are amphoteric in character, they form salts and esters and these salts and esters also form part of the present invention. The nature of such salts and esters is not critical, except that, where they are to be used for medicinal or veterinary purposes, they must be medicinally acceptable, i.e. they must not, or must not to a significant extent, either have increased toxicity or have reduced activity, as compared with the free unsalified or unesterified compound.

Examples of suitable acids for the formation of such salts include: inorganic acids, such as hydrochloric acid, sulfuric acid or phosphoric acid; organic carboxylic acids, such as acetic acid, citric acid, tartaric acid, malonic acid, maleic acid, malic acid, furmaric acid, itaconic acid, citraconic acid or succinic acid; and organic sulfonic acids, such as methanesulfonic acid, benzenesulfonic acid, naphthalenesulfonic acid or p-toluenesulfonic acid.

Examples of suitable esters include: $C_1$–$C_6$, more preferably $C_1$–$C_4$, alkyl esters, for example the methyl, ethyl, propyl, isopropyl, butyl, isobutyl, sec-butyl, t-butyl, pentyl and hexyl esters; aralkyl and diarylalkyl esters, such as the benzyl, p-nitrobenzyl and benzhydryl esters; alkoxycarbonylalkyl esters, in which the alkoxy and alkyl parts are both $C_1$–$C_4$, especially alkoxycarbonylmethyl esters, such as the ethoxycarbonylmethyl and t-butoxycarbonylmethyl esters; alkoxycarbonyloxyalkyl esters in which the alkoxy and alkyl parts are both $C_1$–$C_4$, especially 2-(alkoxycarbonyloxy)ethyl esters, such as the 2-methoxycarbonyloxyethyl, 2-ethoxycarbonyloxyethyl and 2-t-butoxycarbonyloxyethyl esters; and other specific esters, such as the phthalidyl, substituted phthalidyl, phenacyl, substituted phenacyl (e.g. p-nitrophenacyl) and (5-methyl-2-oxo-1,3-dioxolen-4-yl)methyl esters. The esters are preferably formed at the carboxy group.

The carboxy group may also form salts with appropriate bases. The nature of such salts is likewise not critical, provided that, where they are to be used for therapeutic purposes, the salts are pharmaceutically acceptable. Examples of salts with base include: salts with metals, especially alkali metals and alkaline earth metals, such as the lithium, sodium, potassium, calcium and magnesium salts; the ammonium salt; salts with organic amines, such as cyclohexylamine, diisopropylamine or triethylamine; and salts with basic amino acids, such as lysine or arginine.

Where the mureidomycin A, B, C or D is isolated in the form of a salt, it may be converted to the free unsalified compound by conventional means, such as the use of ion-exchange resins or of adsorbents for reverse phase chromatography. Equally, the free unsalified compound may be salified by conventional means. Esters may be prepared by conventional esterification procedures.

The minimal inhibitory concentrations (MIC) of mureidomycins A, B, C and D against various gram-positive and gram-negative bacteria were determined by the two-fold agar dilution method, using a Mueller-Hinton agar medium (produced by Difco). The results are shown in Table 4.

TABLE 4

| Tested Bacterium | MIC (µg/ml) Mureidomycin | | | |
|---|---|---|---|---|
| | A | B | C | D |
| Staphylococcus aureus FDA 209P JC-1 | 200 | >200 | >200 | >200 |
| Escherichia coli NIHJ JC-2 | >200 | >200 | >200 | >200 |
| Proteus mirabilis SANK 70461 | >200 | >200 | >200 | >200 |
| Klebsiella pneumoniae PCI 602 | 25 | 25 | 12.5 | 25 |
| Pseudomonas acidovorans SANK 72782 | >200 | 200 | >200 | 100 |
| Pseudomonas aeruginosa SANK 71873 | 6.25 | 25 | 1.56 | 6.25 |
| Pseudomonas aeruginosa SANK 75775 | 6.25 | 200 | 1.56 | 6.25 |
| Pseudomonas aeruginosa SANK 75175 | 25 | 50 | 3.13 | 12.5 |
| Pseudomonas aeruginosa SANK 70970 | 12.5 | 25 | 1.56 | 3.13 |
| Pseudomonas aeruginosa SANK 73279 | 12.5 | 25 | 1.56 | 6.25 |
| Pseudomonas aeruginosa SANK 73379 | 100 | 200 | 6.25 | 50 |
| Pseudomonas aeruginosa NRRLB 1000 | 25 | 50 | 3.13 | 6.25 |

TABLE 4-continued

| Tested Bacterium | MIC (μg/ml) Mureidomycin | | | |
|---|---|---|---|---|
| | A | B | C | D |
| Pseudomonas aeruginosa ATCC 13388 | 25 | 50 | 3.13 | 6.25 |
| Pseudomonas aeruginosa SANK 70479 | 6.25 | 12.5 | 1.56 | 6.25 |
| Pseudomonas aeruginosa SANK 70579 | <0.1 | 0.2 | <0.1 | 0.2 |
| Pseudomonas aeruginosa SANK 73375 | 12.5 | 25 | 3.13 | 6.25 |
| Pseudomonas aeruginosa NCTC 10490 | 0.4 | 0.8 | 0.4 | 1.56 |
| Serratia marcescens SANK 73060 | >200 | >200 | >200 | >200 |

From the above data, mureidomycins A, B, C and D are active against gram-negative bacteria, particularly against bacteria of the genus Pseudomonas.

No toxicity was observed in mice receiving 400 mg/kg of mureidomycins A, B, C or D intravenously.

From the above findings, it can be seen that mureidomycins A, B, C and D can be used as antibiotics against various diseases caused by bacterial infections. The route of administration can vary widely and may be parenteral (e.g., by subcutaneous, intravenous or intramuscular injection or by suppository) or oral (in which case it may be administered in the form of a tablet, capsule, powder or granule). The dose will, of course, vary with the nature of the disease to be treated, the age, condition and body weight of the patient and the route and time of administration; however, for an adult human patient, a daily dose of from 0.1 to 10 grams is preferred and this may be administered in a single dose or in divided doses.

The invention is further illustrated by the following examples.

EXAMPLE 1

PREPARATION OF ACTIVE METABOLITE

One platinum loopful growth of *Streptomyces flavidovirens* SANK 60486 was inoculated into a 500 ml Erlenmeyer flask containing 80 ml of medium A, which has the following composition (percentages are by weight):

| MEDIUM A | |
|---|---|
| Glucose | 3% |
| Pressed yeast | 1% |
| Soybean meal | 3% |
| Calcium carbonate | 0.4% |
| Magnesium sulfate heptahydrate | 0.2% |
| Anti-foaming agent (Nissan Disfoam CB-442) | 0.01% |
| Water | the balance |
| (pH 7.2 before sterilization) | |

The microorganism was then cultured for 84 hours at 22° C., using a rotary shaker at 220 r.p.m.

25 ml of the resulting seed culture were inoculated into each of four 2-liter Erlenmeyer flasks, each containing 500 ml of medium A, which has the composition described above. The microorganism was then cultured at 22° C. for 24 hours, using a rotary shaker at 220 r.p.m.

The resulting cultured broths were combined. 750 ml of this broth were then inoculated into each of two 30 liter jar fermentors, each containing 15 liters of medium A, and the microorganism was then cultured at 22° C. for 96 hours, whilst aerating at the rate of 15 liters per minute and agitating at 150 r.p.m.

At the end of this time, batches of cultured broth separately cultivated as described above were combined to give a total of 30 liters of cultured broth. Celite 545 (a registered trade mark for a product of Johns-Manville Products Corp, New Jersey, U.S.A.) filter aid was added to the cultured broth and the mixture was filtered, to give 30 liters of a filtrate. This filtrate was adsorbed on 3 liters of Amberlite XAD-2 in a chromatography column. The column was washed, in turn, with 15 liters of purified water and then with 12 liters of water containing 15% v/v methanol, after which it was eluted with 15 liters of water containing 40% v/v methanol. The methanol was then removed from the fractions containing active components by distillation under reduced pressure, after which the residual solution was lyophilized, to give 17.4 g of a crude product as a powder.

17 g of this crude powder were dissolved in 3 liters of purified water, and the solution was passed through a column containing 800 ml of Amberlite CG-50 (H+), to adsorb the active component. The active component was eluted from the column with 0.5M aqueous ammonia. The eluted active fractions (3.5 liters) were collected and concentrated to a volume of 1.0 liter by evaporation under reduced pressure. The concentrate (1.0 liter) was passed through 400 ml of DE-52 ion exchanger (Whatman Ltd.), which had been pre-equilibrated with a 0.1M aqueous solution of ammonium bicarbonate and the active component was adsorbed on the column. The column was eluted with 0.2M aqueous ammonium bicarbonate. The fractions (800 ml) containing the active component were collected and adsorbed on a column containing 200 ml of Diaion HP 20 (Mitsubishi Chemical Industries, Ltd.), after which the column was eluted with 500 ml of 50% v/v aqueous acetone, to give an active component. The fractions containing the active component were concentrated by evaporation under reduced pressure and lyophilized to afford 1.6 g of a crude powdery product containing mureidomycins A, B, C and D.

1.5 g of this crude powder was dissolved in 200 ml of purified water, and the active component was adsorbed on a column containing 500 ml of DE-52 which had been pre-equilibrated with 0.05M aqueous ammonium bicarbonate. The column was washed with 0.05M aqueous ammonium bicarbonate, and then eluted with 0.1M aqueous ammonium bicarbonate, to give fractions, each containing 20 ml of the eluent.

EXAMPLE 2

SEPARATION OF MUREIDOMYCINS A AND C

Fractions No. 80 to 130, from the fractionation described at the end of Example 1, were collected and were adsorbed on a column of Diaion HP 20 in order to desalt them. The desalted eluent was concentrated by evaporation under reduced pressure, and the residue was lyophilized to give 309 mg of a partially purified product, containing mureidomycins A and C, as a powder. 300 mg of this partially purified powder were then subjected to column chromatography through 100 g of silica gel, which was then eluted with a 8:4:1 by volume mixture of butanol, propanol and water, to give fractions, each containing 20 ml of the eluent. The chromatogram showed two peaks due to the presence of two active components.

Fractions No. 13 to 36 were collected, mixed with water and then concentrated by evaporation under reduced pressure and lyophilized to give 33 mg of crude mureidomycin A as a powder.

In a similar manner, 66 mg of crude mureidomycin C were isolated from fractions No. 56 to 75.

EXAMPLE 3
PREPARATION AND PURIFICATION OF MUREIDOMYCIN A

A solution of 30 mg of crude mureidomycin A (prepared as described in Example 2) dissolved in 30% v/v aqueous methanol was adsorbed on a column containing 1000 ml of Toyopearl HW-40, and the column was eluted with 30% v/v aqueous methanol to give fractions, each containing 10 ml of the eluent. Fractions No. 50 to 70 were collected as active fractions, and these were adsorbed on a column containing 10 ml of Amberlite CG50 (H+ type), which was then eluted with 0.5M aqueous ammonia. The fractions containing active components were collected, concentrated by evaporation under reduced pressure and lyophilized to afford 24 mg of mureidomycin A having the properties defined above.

EXAMPLE 4
PREPARATION AND PURIFICATION OF MUREIDOMYCIN C

A solution of 60 mg of crude mureidomycin C (prepared as described in Example 2) dissolved in 30% v/v aqueous methanol was adsorbed on a column containing 1000 ml of Toyopearl HW-40, and the column was eluted with 30% v/v aqueous methanol to give fractions, each containing 10 ml of the eluent. Fractions No. 65 to 85 were collected as active fractions, and these were adsorbed on a column containing 10 ml of Amberlite CG50 (H+ type), which was then eluted with 0.5M aqueous ammonia. The active fractions were collected, concentrated by evaporation under reduced pressure and lyophilized to afford 49 mg of mureidomycin C having the properties defined above.

EXAMPLE 5
SEPARATION OF MUREIDOMYCINS B AND D

Fractions No. 25 to 60, from the fractionation described at the end of Example 1, were collected and were adsorbed on a column of Diaion HP 20 in order to desalt them. The desalted eluent was concentrated by evaporation under reduced pressure, and the residue was lyophilized to give 510 mg of a partially purified product, containing mureidomycins B and D, as a powder.

500 mg of this partially purified powder were subjected to column chromatography through 100 g of silica gel, after which it was eluted with a 8:4:1 by volume mixture of butanol, propanol and water, to give fractions, each containing 20 ml of the eluent. The chromatogram showed two peaks due to the presence of two active components. Fractions No. 37 to 55 were collected, mixed with water and then concentrated by evaporation under reduced pressure and lyophilized to give 74 mg of crude mureidomycin B as a powder. In a similar manner, 67.5 mg of crude mureidomycin D were isolated from fractions No. 76 to 110.

EXAMPLE 6
PREPARATION AND PURIFICATION OF MUREIDOMYCIN B

A solution of 70 mg of crude mureidomycin B (prepared as described in Example 5) dissolved in 30% v/v aqueous methanol was adsorbed on a column containing 1000 ml of Toyopearl HW-40, and the column was eluted with 30% v/v aqueous methanol to give fractions, each containing 10 ml of the eluent. Fractions No. 55 to 75 were collected as active fractions, and these were adsorbed on a column containing 10 ml of Amberlite CG50 (H+ type) and eluted with 0.5M aqueous ammonia. The fractions containing active components were collected, concentrated by evaporation under reduced pressure and lyophilized to afford 45 mg of mureidomycin B having the properties defined above.

EXAMPLE 7
PREPARATION AND PURIFICATION OF MUREIDOMYCIN D

A solution of 65 mg of crude mureidomycin D (prepared as described in Example 5) dissolved in 30% v/v aqueous methanol was adsorbed on a column containing 1000 ml of Toyopearl HW-40, and the column was eluted with 30% v/v aqueous methanol to give fractions, each containing 10 ml of the eluent. Fractions No. 65 to 85 were collected as active fractions, and these were then adsorbed on a column containing 10 ml of Amberlite CG50 (H+ type) and eluted with 0.5M aqueous ammonia. The fractions were collected, concentrated by evaporation under reduced pressure and lyophilized to afford 40 mg of mureidomycin D having the properties defined above.

EXAMPLE 8
CAPSULES FOR ORAL ADMINISTRATION

The following powders were mixed:

| | |
|---|---|
| Mureidomycin A | 100 mg |
| Lactose | 100 mg |
| Maize starch | 148.5 mg |
| Magnesium stearate | 1.5 mg |
| | 350 mg | and passed through a 30-mesh sieve (Tyler standard). The mixture (350 mg) was sealed into a gelatin capsule No. 2 to yield the desired capsule.

EXAMPLE 9
CAPSULES FOR ORAL ADMINISTRATION

The following powders were mixed:

| | |
|---|---|
| Mureidomycin C | 100 mg |
| Lactose | 100 mg |
| Maize starch | 148.5 mg |
| Magnesium stearate | 1.5 mg |
| | 350 mg | and passed through a 30-mesh sieve (Tyler standard). The mixture (350 mg) was sealed into a gelatin capsule No. 2 to yield the desired capsule.

EXAMPLE 10

INJECTION 1.0 g of mureidomycin A was dissolved in 5.0 ml of a 1/15M phosphate buffer solution and the solution was sealed into a 5 ml ampoule. The ampoule was sterilized by a conventional procedure to yield the desired injectible liquid.

EXAMPLE 11

INJECTION 1.0 g of mureidomycin C was dissolved in 5.0 ml of a 1/15M phosphate buffer solution and the solution was sealed into a 5 ml ampoule. The ampoule was sterilized by a conventional procedure to yield the desired injectible liquid.

EXAMPLE 12

CAPSULES FOR ORAL ADMINISTRATION

The following powders were mixed:

| | |
|---|---|
| Mureidomycin B | 100 mg |
| Lactose | 100 mg |
| Maize starch | 148.5 mg |
| Magnesium stearate | 1.5 mg |
| | 350 mg | and passed through a 30-mesh sieve (Tyler standard). The mixture (350 mg) was sealed into a gelatin capsule No. 2 to yield the desired capsule.

EXAMPLE 13

CAPSULES FOR ORAL ADMINISTRATION

The following powders were mixed:

| | |
|---|---|
| Mureidomycin D | 100 mg |
| Lactose | 100 mg |
| Maize starch | 148.5 mg |
| Magnesium stearate | 1.5 mg |
| | 350 mg | and passed through a 30-mesh sieve (Tyler standard). The mixture (350 mg) was sealed into a gelatin capsule No. 2 to yield the desired capsule.

EXAMPLE 14

INJECTION 1.0 g of mureidomycin B was dissolved in 5.0 ml of a 1/15M phosphate buffer solution and the solution was sealed into a 5 ml ampoule. The ampoule was sterilized by a conventional procedure to yield the desired injectible liquid.

EXAMPLE 15

INJECTION 1.0 g of mureidomycin D was dissolved in 5.0 ml of a 1/15M phosphate buffer solution and the solution was sealed into a 5 ml ampoule. The ampoule was sterilized by a conventional procedure to yield the desired injectible liquid.

We claim:

1. Compounds mureidomycin A, B, C and D of the formula

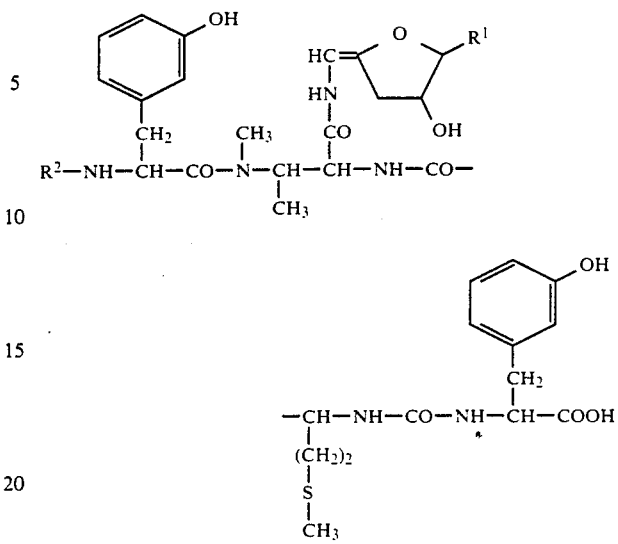

wherein:

for mureidomycin A, $R^1$ represents a uracil group and $R^2$ represents a hydrogen atom; for mureidomycin B, $R^1$ represents a dihydrouracil group and $R^2$ represents a hydrogen atom; for mureidomycin C, $R^1$ represents a uracil group and $R^2$ represents a glycine group; and for mureidomycin D, $R^1$ represents a dihydrouracil group and $R^2$ represents a glycine group; and pharmaceutically acceptable salts and pharmaceutically acceptable esters thereof.

2. The compound of claim 1 which is mureidomycin A and pharmaceutically acceptable salts and pharmaceutically acceptable esters thereof.

3. The compound of claim 1 which is mureidomycin B and pharmaceutically acceptable salts and pharmaceutically acceptable esters thereof.

4. The compound of claim 1 which is mureidomycin C and pharmaceutically acceptable salts and pharmaceutically acceptable esters thereof.

5. The compound of claim 1 which is mureidomycin D and pharmaceutically acceptable salts and pharmaceutically acceptable esters thereof.

Figure 1B:
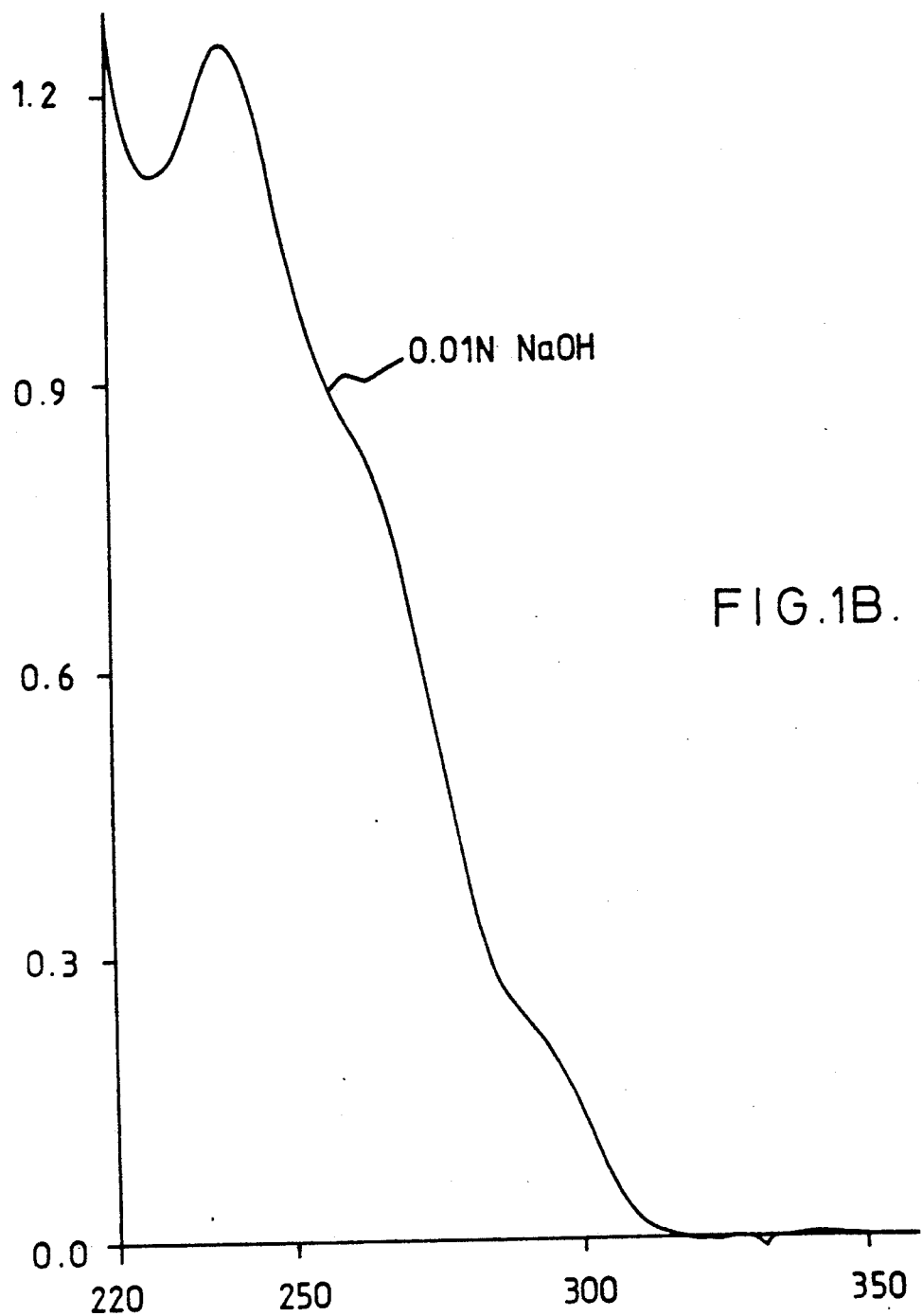
Figure 2:
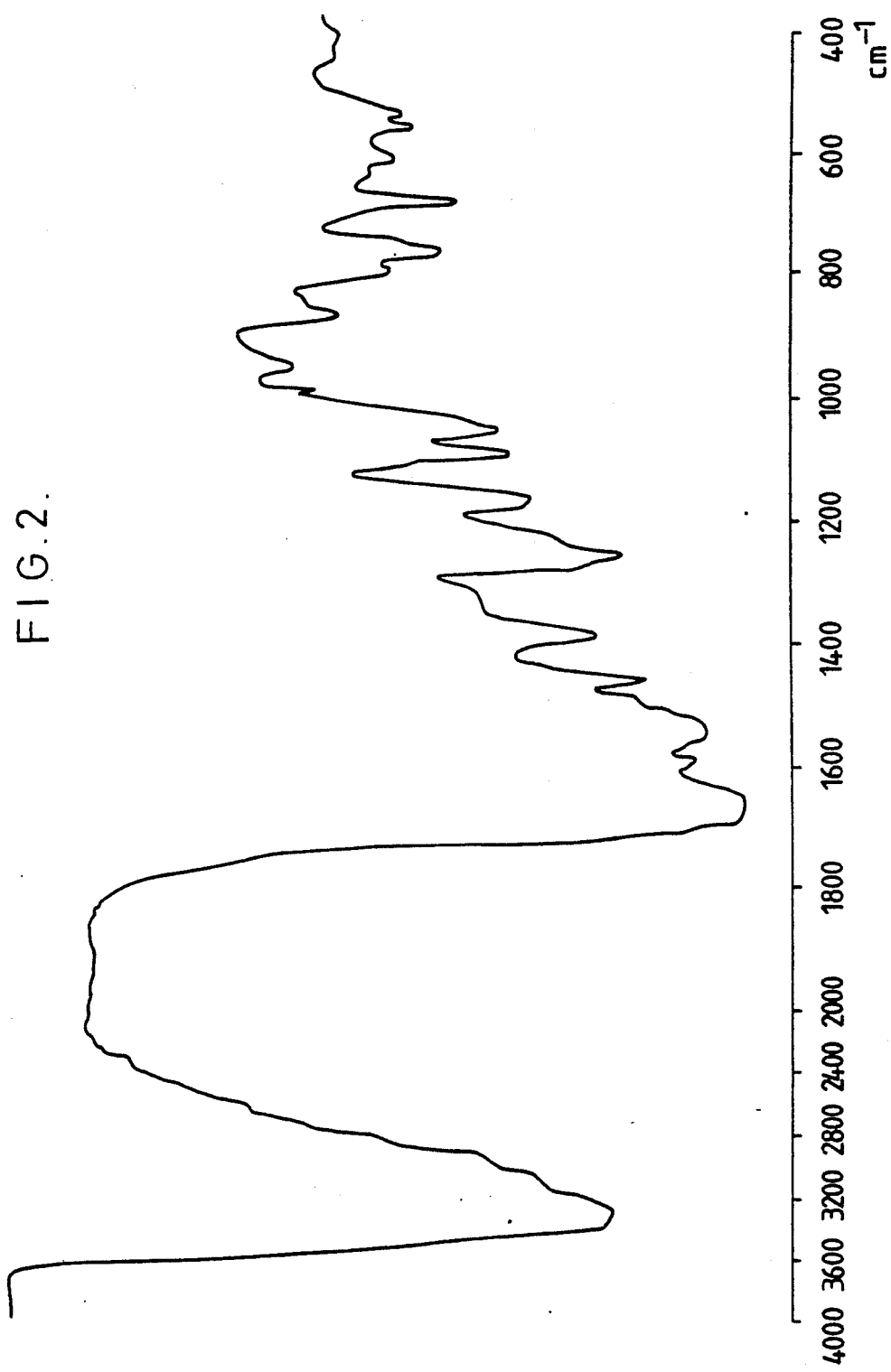
FIG. 2 shows the infrared absorption spectrum of mureidomycin A.
Figure 3:
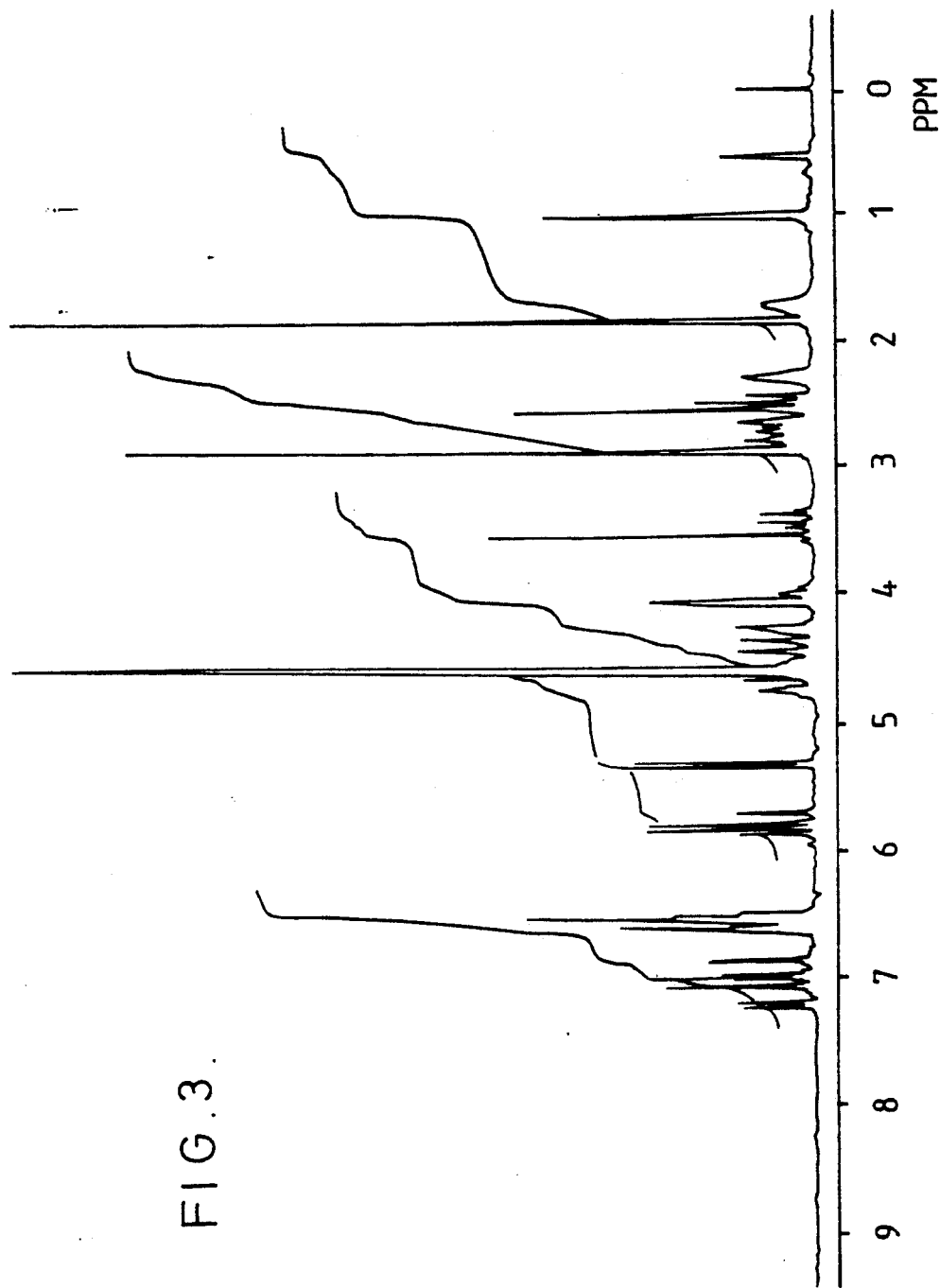
FIG. 3 shows the nuclear magnetic resonance spectrum of mureidomycin A.

6. The compound mureidomycin A of claim 2 which is characterized by the following physico-chemical properties:

1) Character and appearance: Amphoteric, soluble in water, white powder;
2) Specific rotation: $[\alpha]_D^{25} = +40.9°$ (c=0.69, 50% v/v aqueous methanol);
3) Elemental analysis: C, 49.73%; H, 5.65%; N, 12.08%; S, 3.40% - measured as the hydrate;
4) Molecular weight: 840 (high resolution mass spectrum), FAB MS: 841.31798 (QM+) (FAB MS is Fast Atom Bombardment Mass Spectroscopy);
5) Molecular formula: $C_{38}H_{48}N_8O_{12}S_1$;
6) Products resulting from acid hydrolysis: Uracil, m-tyrosine, 2-amino-3-N-methylaminobutyric acid;
7) Ultraviolet absorption spectrum: $\lambda_{max}$ nm ($E_1^{1\%}$ cm) 260 nm (348) in neutral water; 258 nm (358) in 0.01N aqueous HCl; 240 nm (499), 265 nm (330, shoulder) and 295 nm (78, shoulder) in 0.01N aqueous NaOH; the spectra are shown in FIGS. 1A and 1B of the accompanying drawings;

8) Infrared absorption spectrum (KBr), $\nu_{max}$ cm$^{-1}$; the spectrum measured in a KBr disk is shown in FIG. 2 of the accompanying drawings;

9) Nuclear magnetic resonance spectrum, δ ppm: the spectrum (400 MHz) was measured in dimethyl sulfoxide using TMS (tetramethylsilane) as an external standard and is shown in FIG. 3 of the accompanying drawings;

10) Solubility: Soluble in water and methanol, slightly soluble in acetone, and insoluble in ethyl acetate, chloroform and benzene;

11) Color reaction: Positive to ninhydrin, sulfuric acid, iodine, ferric chloride and Baeyer reactions;

12) Thin-layer chromatography:
Rf value; 0.36
Adsorbent; Silica gel plate (Merck, Kieselgel 60 F$_{254}$)
Developing solvent: a 4:2:1 by volume mixture of butanol, propanol and water;

13) High performance liquid chromatography:
Column: Aquasil SS 372-N (Senshu Kagaku Co.)
Developing solvent; a 200:100:100:40 by volume mixture of chloroform, isopropanol, methanol and water;
Flow rate: 1 ml/minute;
Retention time: 3.92 minutes;
and pharmaceutically acceptable salts and pharmaceutically acceptable esters thereof.

Figure 7:
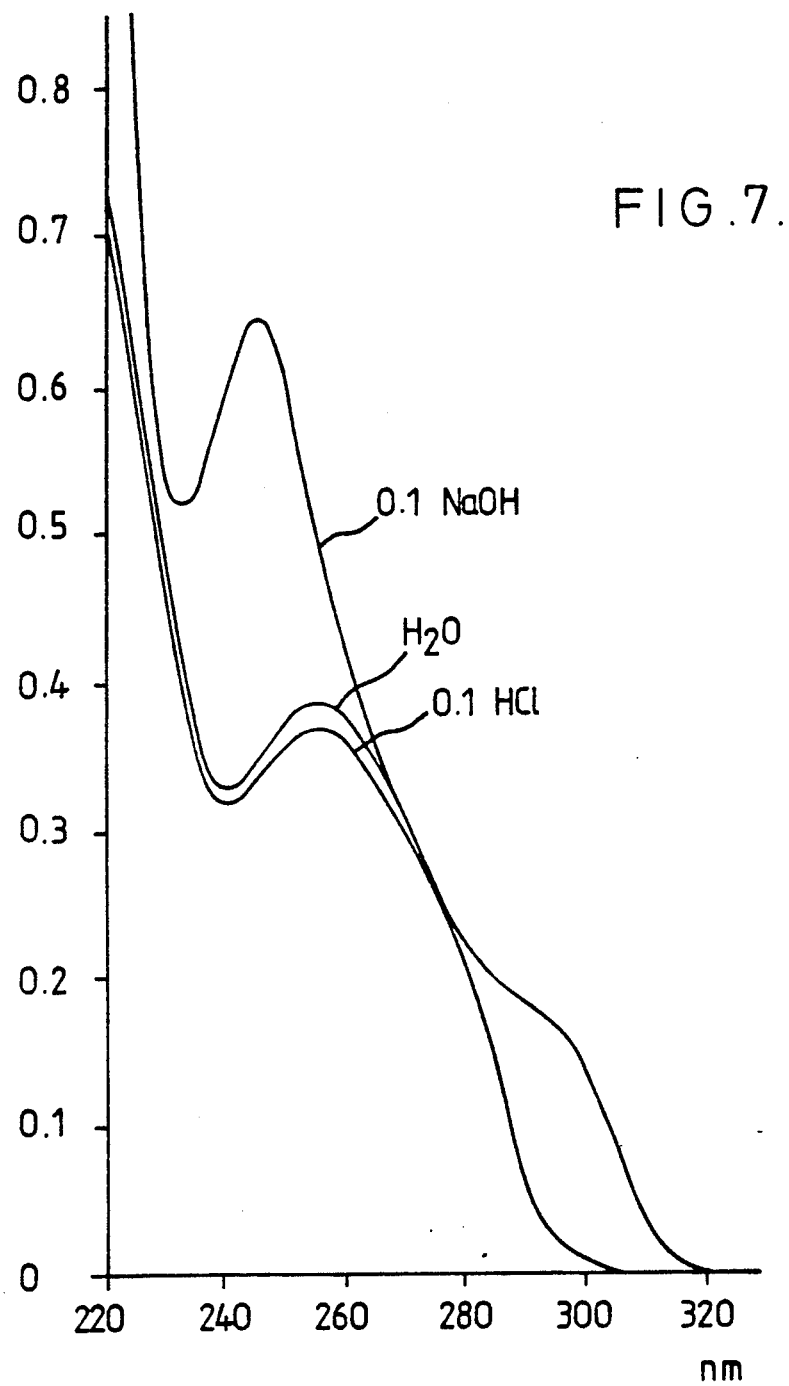
FIG. 7 shows the ultraviolet absorption spectrum of mureidomycin B.
Figure 8:
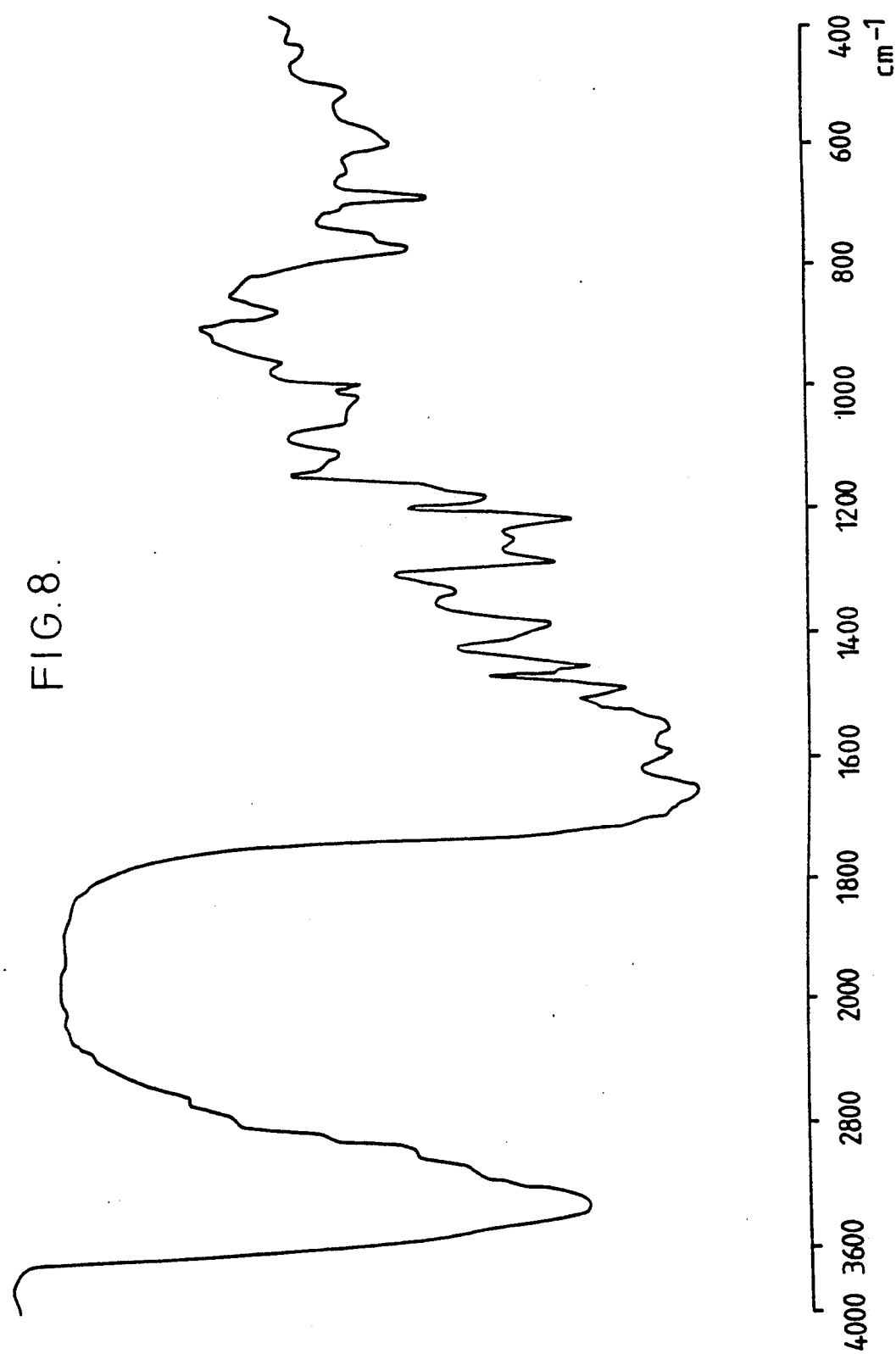
FIG. 8 shows the infrared absorption spectrum of mureidomycin B.
Figure 9:
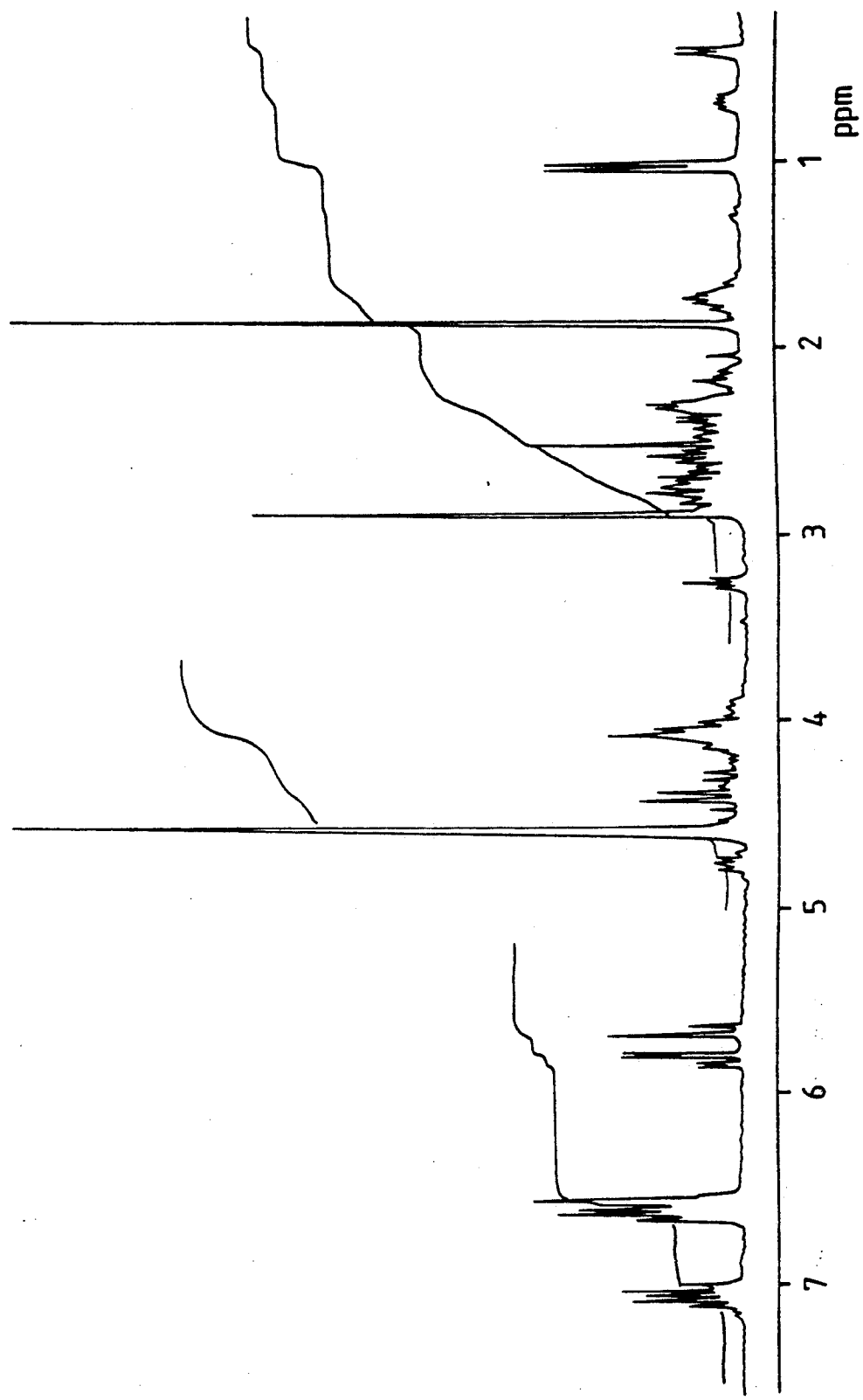
FIG. 9 shows the nuclear magnetic resonance spectrum of mureidomycin B.

7. The compound mureidomycin B of claim 3 which is characterised by the following physico-chemical properties:
1) Character and appearance: Amphoteric, soluble in water, white powder;
2) Specific rotation: $[\alpha]_D^{23} = -7°$ (c=0.3, 50% v/v aqueous methanol);
3) Elemental analysis: C, 50.67%; H, 6.36%; N, 12.62%; S, 3.13%—measured as the hydrate;
4) Molecular weight: 842 (high resolution mass spectrum), FAB MS: 843.33289 (QM$^+$);
5) Molecular formula: $C_{38}H_{50}N_8O_{12}S_1$;
6) Products resulting from acid hydrolysis: Dihydrouracil, m-tyrosine, 2-amino-3-N-methylaminobutyric acid;
7) Ultraviolet absorption spectrum: $\lambda_{max}$ nm (E$_1^{1\%}$ cm) 255 nm (194) in neutral water; 255 nm (186) in 0.1N aqueous HCl; 245 nm (325) and 295 nm (85, shoulder) in 0.1N aqueous NaOH; the spectrum is shown in FIG. 7 of the accompanying drawings;
8) Infrared absorption spectrum (KBr) $\nu_{max}$ cm$^{-1}$: the spectrum measured in a KBr disk is shown in FIG. 8 of the accompanying drawings;
9) Nuclear magnetic resonance spectrum, δ ppm: the spectrum (270 MHz) was measured in deuterium oxide using TMS as an external standard and is shown in FIG. 9 of the accompanying drawings;
10) Solubility: Soluble in water and methanol, slightly soluble in acetone, and insoluble in ethyl acetate, chloroform and benzene;
11) Color reaction: Positive to ninhydrin, sulfuric acid, iodine, ferric chloride and Baeyer reactions;
12) Thin-layer chromatography:
Rf value: 0.34
Adsorbent: Silica gel plate (Merck, Kieselgel 60 F$_{254}$)
Developing solvent: a 4:2:1 by volume mixture of butanol, propanol and water;
13) High performance liquid chromatography:
Column: Aquasil SS 372-N (Senshu Kagaku Co.)
Developing solvent: a 200:100:100:40 by volume mixture of chloroform, isopropanol, methanol and water
Flow rate: 1 ml/minute;
Retention time: 3.94 minutes;
and pharmaceutically acceptable salts and pharmaceutically acceptable esters thereof.

Figure 4A:
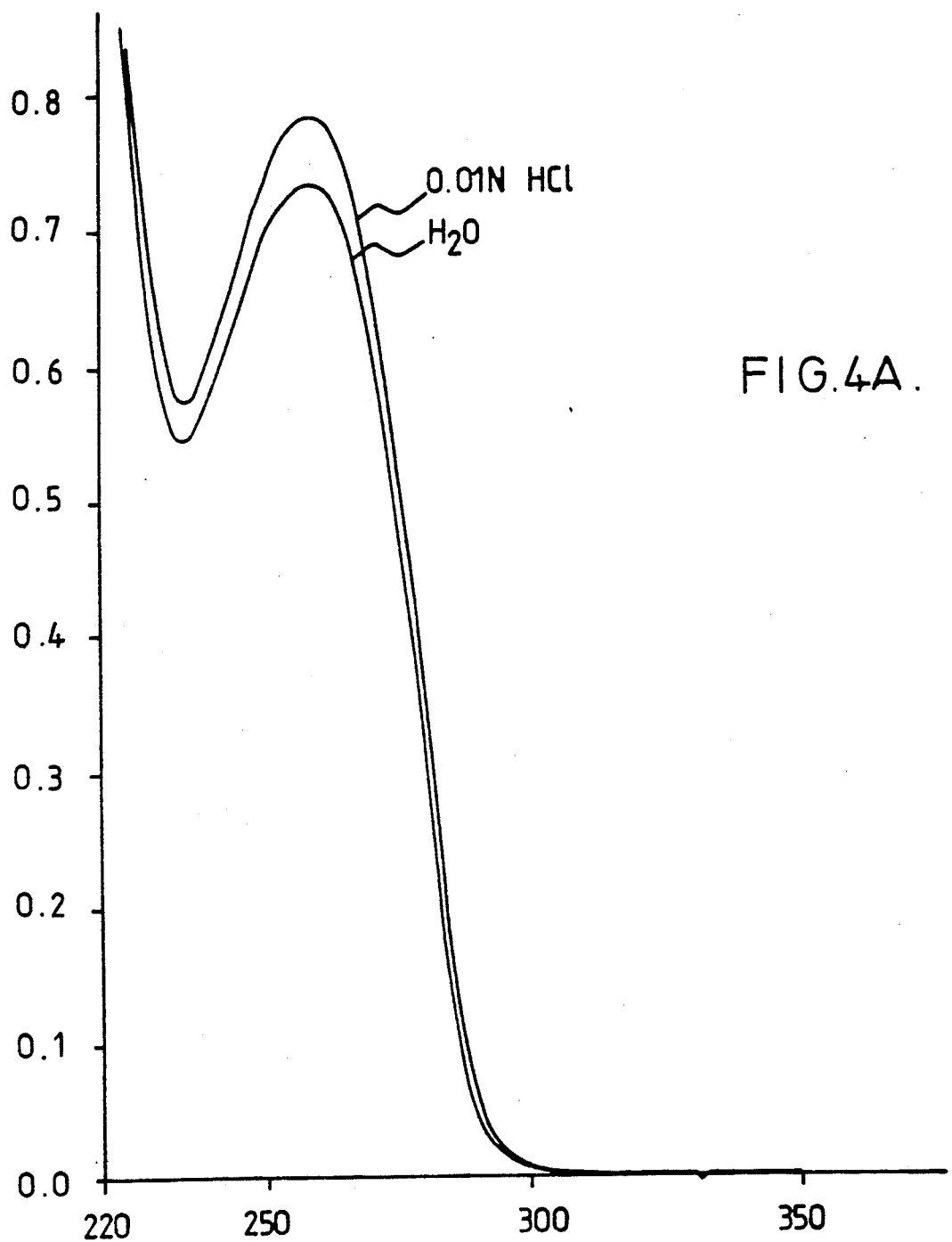
FIG. 4 shows the ultraviolet absorption spectrum of mureidomycin C.
Figure 4B:
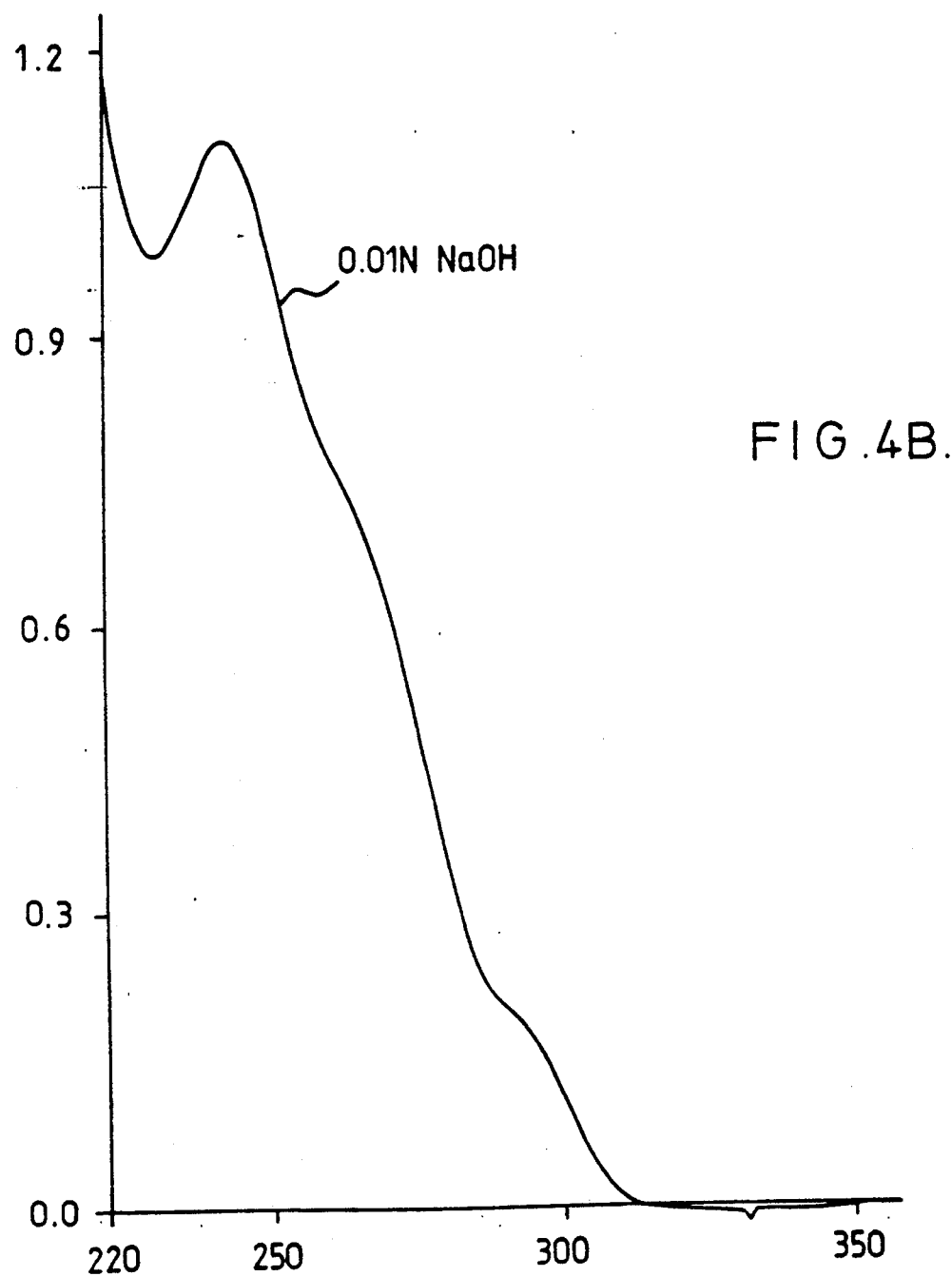
Figure 5:
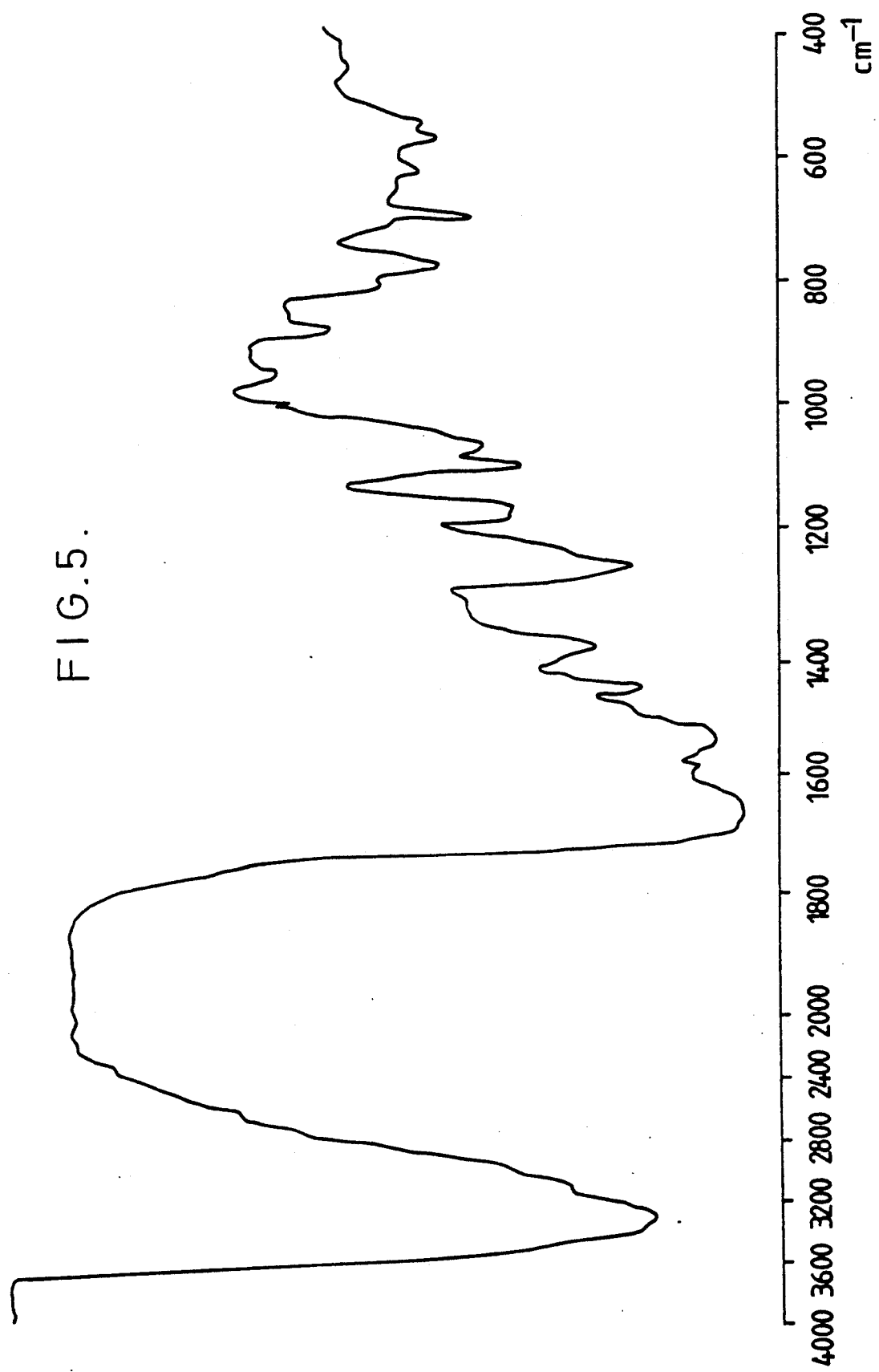
FIG. 5 shows the infrared absorption spectrum of mureidomycin C.
Figure 6:
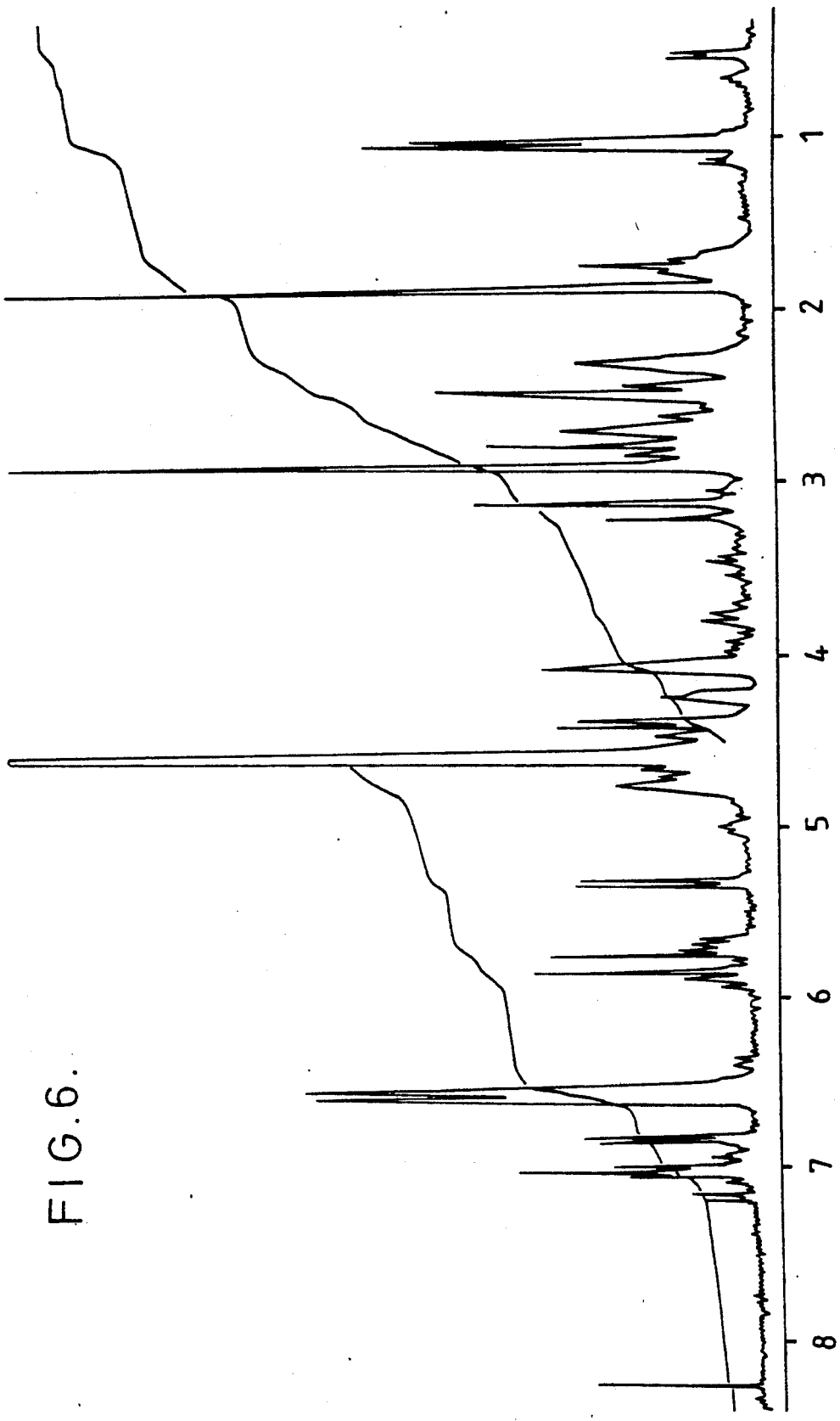
FIG. 6 shows the nuclear magnetic resonance spectrum of mureidomycin C.

8. The compound mureidomycin C of claim 4 which is characterised by the following physico-chemical properties:
1) Character and appearance: Amphoteric, soluble in water, white powder;
2) Specific rotation: $[\alpha]_D^{25} = +16.7°$ (c=0.57, 50% v/v aqueous methanol);
3) Elemental analysis: C, 49.44%; H, 5.50%; N, 12.53%; S, 3.09%—measured as the hydrate;
4) Molecular weight: 897 (high resolution mass spectrum), FAB MS: 898.33687 (QM$^+$);
5) Molecular formula: $C_{40}H_{51}N_9O_{13}S_1$;
6) Products resulting from acid hydrolysis: Uracil, glycine, m-tyrosine, 2-amino-3-N-methylaminobutyric acid;
7) Ultraviolet absorption spectrum: $\lambda_{max}$ nm (E$_1^{1\%}$ cm) 258 nm (292) in neutral water; 259 nm (312) in 0.01N aqueous HCl; 240 nm (444), 265 nm (276, shoulder) and 295 nm (72, shoulder) in 0.01N aqueous NaOH; the spectra are shown in FIGS. 4A and 4B of the accompanying drawings;
8) Infrared absorption spectrum (KBr) $\nu_{max}$ cm$^{-1}$: the spectrum measured in a KBr disk is shown in FIG. 5 of the accompanying drawings;
9) Nuclear magnetic resonance spectrum, δ ppm: the spectrum (270 MHz) was measured in deuterium oxide using TMS as an external standard and is shown in FIG. 6 of the accompanying drawings;
10) Solubility: Soluble in water and methanol, slightly soluble in acetone, and insoluble in ethyl acetate, chloroform and benzene;
11) Color reaction: Positive to ninhydrin, sulfuric acid, iodine, ferric chloride and Baeyer reactions;
12) Thin-layer chromatography:
Rf value: 0.29
Absorbent: Silica gel plate (Merck, Kieselgel 60 F$_{254}$)
Developing solvent: a 4:2:1 by volume mixture of butanol, propanol and water;
13) High performance liquid chromatography:
Column: Aquasil SS 372-N (Senshu Kagaku Co.)
Developing solvent: a 200:100:100:40 by volume mixture of chloroform, isopropanol, methanol and water
Flow rate: 1 ml/minute;
Retention time: 6.29 minutes; and pharmaceutically acceptable salts and pharmaceutically acceptable esters thereof.

Figure 10:
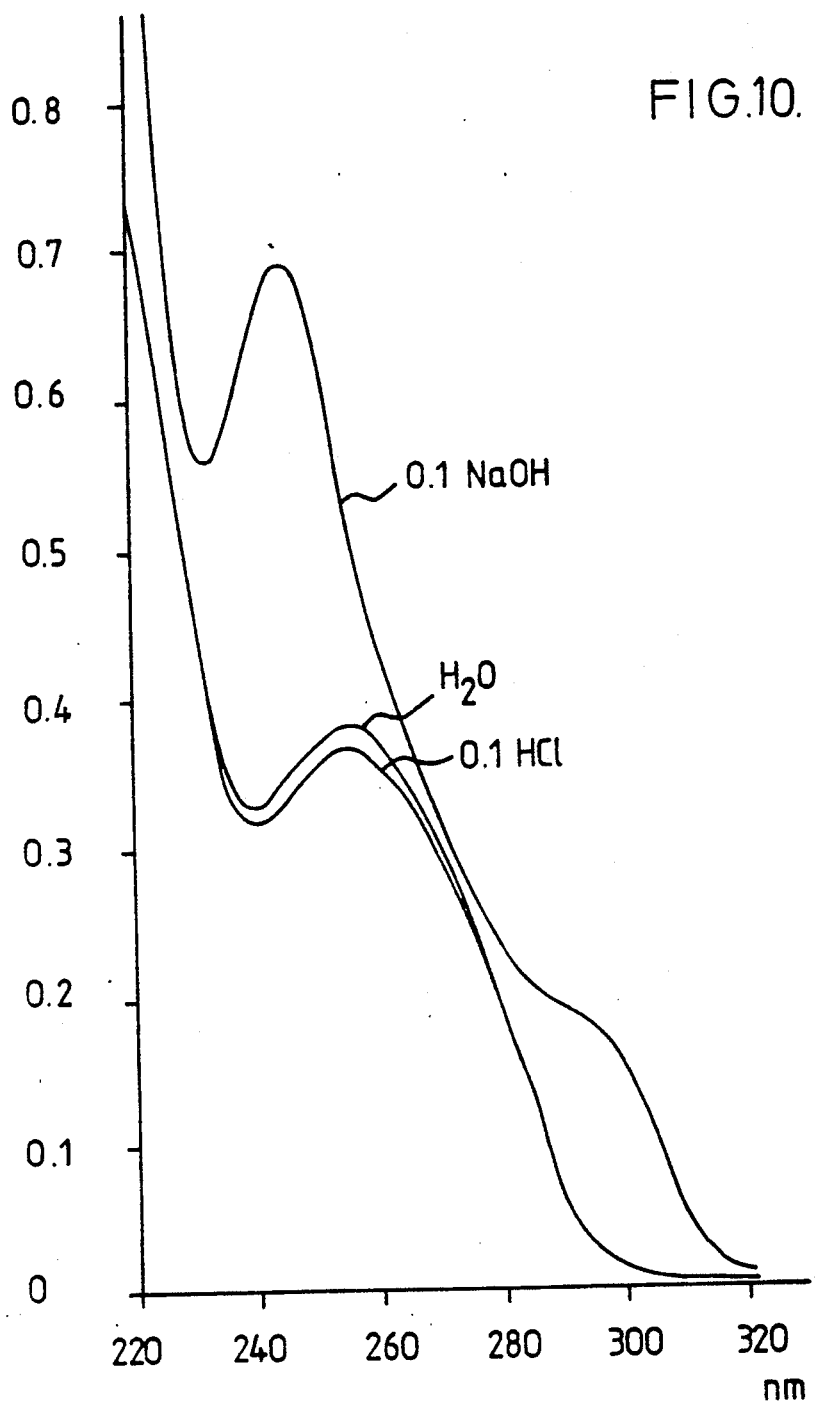
FIG. 10 shows the ultraviolet absorption spectrum of mureidomycin D.
Figure 11:
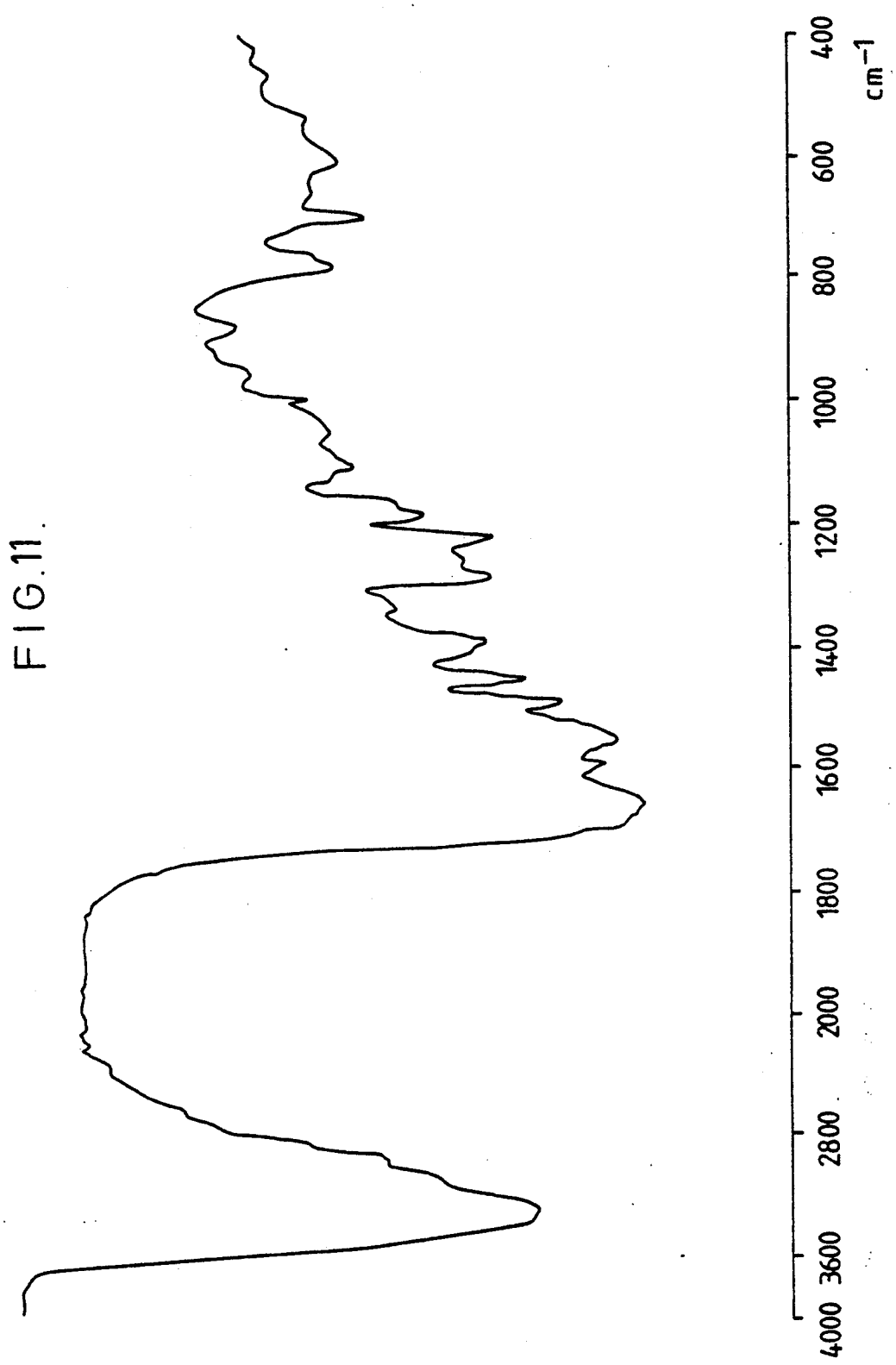
FIG. 11 shows the infrared absorption spectrum of mureidomycin D.
Figure 12:
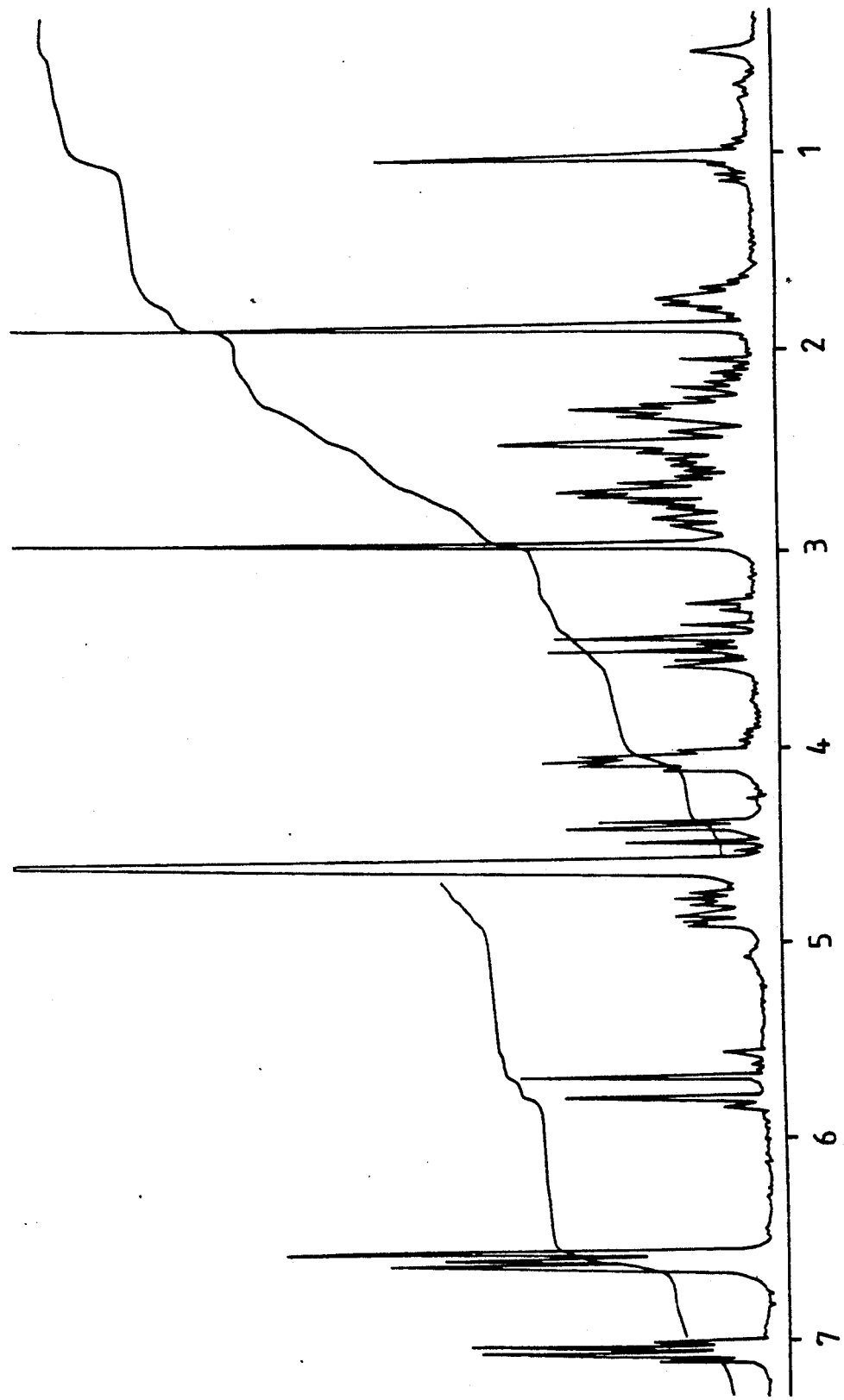
FIG. 12 shows the nuclear magnetic resonance spectrum of mureidomycin D.

9. The compound mureidomycin D of claim 5 which is characterised by the following physico-chemical properties:
1) Character and appearance: Amphoteric, soluble in water, white powder;
2) Specific rotation: $[\alpha]_D^{23} = -30°$ (c=0.52, 50% v/v aqueous methanol);
3) Elemental analysis: C, 48.79%; H, 5.86%; N, 12.42%; S, 3.26%—measured as the hydrate;
4) Molecular weight: 899 (high resolution mass spectrum), FAB MS: 900.35617 (QM$^+$);
5) Molecular formula: $C_{40}H_{53}N_9O_{13}S_1$;

6) Products resulting from acid hydrolysis: Dihydrouracil, glycine, m-tyrosine, 2-amino-3-N-methylaminobutyric acid;
7) Ultraviolet absorption spectrum: $\lambda_{max}$ nm ($E_1^{1\%}{}_{cm}$) 255 nm (191) in neutral water; 255 nm (184) in 0.1N aqueous HCl; 245 nm (346), and 295 nm (90, shoulder) in 0.1N aqueous NaOH; the spectrum is shown in FIG. 10 of the accompanying drawings;
8) Infrared absorption spectrum (KBr) $v_{max}$ cm$^{-1}$: the spectrum measured in a KBr disk is shown in FIG. 11 of the accompanying drawings;
9) Nuclear magnetic resonance spectrum, δ ppm: the spectrum (270 MHz) was measured in deuterium oxide using TMS as an external standard and is shown in FIG. 12 of the accompanying drawings;
10) Solubility: Soluble in water and methanol, slightly soluble in acetone and insoluble in ethyl acetate, chloroform and benzene;
11) Color reaction: Positive to ninhydrin, sulfuric acid, iodine, ferric chloride and Baeyer reactions;
12) Thin-layer chromatography: Rf value: 0.26
   Adsorbent: Silica gel plate (Merck, Kieselgel 60 F$_{254}$)
   Developing solvent: a 4:2:1 by volume mixture of butanol, propanol and water;
13) High performance liquid chromatography:
   Column: Aquasil SS 372-N (Senshu Kagaku Co.)
   Developing solvent: a 200:100:100:40 by volume mixture of chloroform, isopropanol, methanol and water
   Flow rate: 1 ml/minute;
   Retention time: 7.24 minutes;

10. A pharmaceutical composition comprising an effective antibiotic amount of mureidomycin A, of claim 2, or a pharmaceutically acceptable salt or a pharmaceutically acceptable ester thereof in admixture with a pharmaceutically acceptable carrier or diluent.

11. A method for the treatment of prophylaxis of bacterial infections by administering an effective antibiotic amount of mureidomycin A, of claim 2, or a pharmaceutically acceptable salt or a pharmaceutically acceptable ester thereof to an animal.

12. A pharmaceutical composition comprising an effective antibiotic amount of mureidomycin B, of claim 3, or a pharmaceutically acceptable salt or a pharmaceutically effective ester thereof in admixture with a pharmaceutically acceptable carrier or diluent.

13. A method for the treatment or prophylaxis of bacterial infections by administering an effective antibiotic amount of mureidomycin B, of claim 3, or a pharmaceutically effective salt or a pharmaceutically effective ester thereof to an animal.

14. A pharmaceutical composition comprising an effective antibiotic amount of mureidomycin C, of claim 4, or a pharmaceutically acceptable salt or a pharmaceutically acceptable ester thereof in admixture with a pharmaceutically acceptable carrier or diluent.

15. A method for the treatment of prophylaxis of bacterial infections by administering an effective antibiotic amount of mureidomycin C, of claim 4, or a pharmaceutically acceptable salt or a pharmaceutically acceptable ester thereof to an animal.

16. A pharmaceutical composition comprising an effective antibiotic amount of mureidomycin D, of claim 5, or a pharmaceutically acceptable salt or a pharmaceutically acceptable ester thereof in admixture with a pharmaceutically acceptable carrier or diluent.

17. A method for the treatment or prophylaxis of bacterial infections by administering an effective antibiotic amount of mureidomycin D, of claim 5, or a pharmaceutically acceptable salt of a pharmaceutically acceptable ester thereof to an animal.

18. The compound of claim 6, wherein the ester is selected from the group consisting of $C_1$-$C_6$ alkyl esters, aralkyl esters, alkoxycarbonylalkyl esters in which the alkoxy and alkyl moieties each have 1 to 4 carbon atoms, alkoxycarbonyloxyalkyl esters in which the alkoxy and alkyl moieties each have 1 to 4 carbon atoms, phthalidyl esters, phenacyl esters, and (5-methyl-2-oxo-1,3-dioxolen-4-yl) methyl esters.

19. The compound of claim 6, wherein the ester is selected from the group consisting of methyl ester, ethyl ester, propyl ester, isopropyl ester, butyl ester, isobutyl ester, sec-butyl ester, t-butyl ester, pentyl ester, hexyl ester, benzyl ester, p-nitrobenzyl ester, benzhydryl ester, ethoxycarbonylmethyl ester, t-butoxycarbonylmethyl ester, 2-(alkoxycarbonyloxy)ethyl ester and p-nitrophenacyl ester.

20. The compound of claim 1, wherein the ester is selected from the group consisting of $C_1$-$C_6$ alkyl esters, aralkyl esters, alkoxycarbonylalkyl esters in which the alkoxy and alkyl moieties each have 1 to 4 carbon atoms, alkoxycarbonyloxyalkyl esters in which the alkoxy and alkyl moieties each have 1 to 4 carbon atoms, phthalidyl esters, substituted phthalidyl esters, phenacyl esters, substituted phenacyl esters and (5-methyl-2-oxo-1,3-dioxolen-4-yl) methyl esters.

21. The compound of claim 1, wherein the ester is selected from the group consisting of methyl ester, ethyl ester, propyl ester, isopropyl ester, butyl ester, isobutyl ester, sec-butyl ester, t-butyl ester, pentyl ester, hexyl ester, benzyl ester, p-nitrobenzyl ester, benzhydryl ester, ethoxycarbonylmethyl ester, t-butoxycarbonylmethyl ester, 2-(alkoxycarbonyloxy)ethyl ester and p-nitrophenacyl ester.

22. The method of claim 11, wherein said mureidomycin A is administered in a daily dose of 0.1 to 10 grams.

23. The method of claim 13, wherein said mureidomycin B is administered in a daily dose of 0.1 to 10 grams.

24. The method of claim 15, wherein said mureidomycin C is administered in a daily dose of 0.1 to 10 grams.

25. The method of claim 17, wherein said mureidomycin D is administered in a daily dose of 0.1 to 10 grams.

* * * * *

UNITED STATES PATENT AND TRADEMARK OFFICE
CERTIFICATE OF CORRECTION

PATENT NO. : 5,039,663
DATED : August 13, 1991
INVENTOR(S) : HANEISHI et al It is certified that error appears in the above-identified patent and that said Letters Patent is hereby corrected as shown below:

Column 20, Claim 20 -

Line 36, delete "substituted phthalidyl esters".

Line 37, delete "substituted phenacyl esters".

Signed and Sealed this

Eighteenth Day of May, 1993

Attest:

MICHAEL K. KIRK

Attesting Officer

Acting Commissioner of Patents and Trademarks